(12) United States Patent
Gardner et al.

(10) Patent No.: US 11,382,308 B2
(45) Date of Patent: Jul. 12, 2022

(54) APPARATUS AND METHODS FOR SAMPLING

(71) Applicant: SNPSHOT TRUSTEE LIMITED, Auckland (NZ)

(72) Inventors: Michael Stuart Gardner, Auckland (NZ); Roy Victor Bladen, Auckland (NZ); Rory Bladen, Auckland (NZ)

(73) Assignee: SNPSHOT TRUSTEE LIMITED, Auckland (NZ)

( * ) Notice: Subject to any disclaimer, the term of this patent is extended or adjusted under 35 U.S.C. 154(b) by 639 days.

(21) Appl. No.: 16/090,552

(22) PCT Filed: Mar. 31, 2017

(86) PCT No.: PCT/IB2017/051840
§ 371 (c)(1),
(2) Date: Oct. 1, 2018

(87) PCT Pub. No.: WO2017/168374
PCT Pub. Date: Oct. 5, 2017

(65) Prior Publication Data
US 2019/0110436 A1    Apr. 18, 2019

(30) Foreign Application Priority Data

Mar. 31, 2016  (NZ) .......................... 718586
Oct. 10, 2016  (NZ) .......................... 725097
Nov. 2, 2016   (NZ) .......................... 725831

(51) Int. Cl.
*A61B 5/00*    (2006.01)
*A01K 11/00*   (2006.01)
(Continued)

(52) U.S. Cl.
CPC .......... *A01K 11/003* (2013.01); *A01K 11/004* (2013.01); *A61B 10/0096* (2013.01);
(Continued)

(58) Field of Classification Search
CPC .... A01K 11/003; A01K 11/004; A61B 10/00; A61B 90/98; A61B 10/0233;
(Continued)

(56) References Cited

U.S. PATENT DOCUMENTS 5,468,968 A    11/1995  Bailey et al.
5,511,556 A     4/1996  DeSantis
(Continued)

FOREIGN PATENT DOCUMENTS

AU    2003272940 A1    5/2004
CN        1275894 A   12/2000
(Continued)

OTHER PUBLICATIONS

PCT/IB2017/051840 International Search Report and Written Opinion of the International Searching Authority dated May 26, 2017 (21 pages).

(Continued)

*Primary Examiner* — May A Abouelela
(74) *Attorney, Agent, or Firm* — Michael Best & Friedrich LLP

(57) ABSTRACT

A sampling system that uses a handheld body that can hold a punch and storage container to receive the punch. A sample identification reader and an item ID reader are used to read ID of the item and punch or storage container. The timing between the taking of a sample and the reading of the item ID and the ID of the punch/storage container may be recorded and if the time is too long the sample may be assigned as being invalid or of high tamper risk.

15 Claims, 13 Drawing Sheets

(51) Int. Cl.
   *A61B 10/00* (2006.01)
   *A61B 10/02* (2006.01)
   *A61B 90/98* (2016.01)
   *A61F 13/38* (2006.01)

(52) U.S. Cl.
   CPC .......... *A61B 10/0233* (2013.01); *A61B 90/98* (2016.02); *A61F 13/38* (2013.01); *A61B 2010/0208* (2013.01); *A61B 2503/40* (2013.01)

(58) Field of Classification Search
   CPC . A61B 2562/08; A61B 10/02; A61B 10/0096; A61B 2503/40; A61B 2010/0208; G16H 10/40; A61F 13/38
   USPC ........................................................ 600/567
   See application file for complete search history.

(56) References Cited

U.S. PATENT DOCUMENTS

| | | | |
|---|---|---|---|
| 5,591,974 A | | 1/1997 | Troyer et al. |
| 6,659,338 B1* | | 12/2003 | Dittmann ............ A01K 11/003 235/375 |
| 6,947,866 B2* | | 9/2005 | Staab .................... G01N 1/02 235/375 |
| 2002/0137033 A1 | | 9/2002 | Brem |
| 2002/0143320 A1* | | 10/2002 | Levin ................ G06K 17/0029 606/1 |
| 2005/0051109 A1 | | 3/2005 | Fantin et al. |
| 2005/0187733 A1 | | 8/2005 | Stabb |
| 2006/0108218 A1* | | 5/2006 | Gephart ............. A61B 5/14546 204/400 |
| 2006/0110253 A1 | | 5/2006 | Chen |
| 2006/0116603 A1* | | 6/2006 | Shibazaki ......... A61B 10/0096 600/562 |
| 2006/0199169 A1* | | 9/2006 | Lam ...................... G01N 1/286 435/4 |
| 2008/0064983 A1* | | 3/2008 | Stromberg ........... A01K 11/003 600/567 |
| 2008/0221456 A1* | | 9/2008 | Babchenko .......... A61B 5/6848 600/476 |
| 2008/0227662 A1* | | 9/2008 | Stromberg ........... A01K 11/003 506/39 |
| 2010/0018469 A1* | | 1/2010 | Gottschling ......... A01K 11/003 119/174 |
| 2010/0063847 A1* | | 3/2010 | Eisenberg .......... A61B 10/0096 705/3 |
| 2010/0088116 A1* | | 4/2010 | Eisenberg ............... G16H 10/40 705/3 |
| 2012/0130275 A1* | | 5/2012 | Chudzik ............ A61B 10/0283 600/567 |
| 2014/0376762 A1* | | 12/2014 | Lipman ............ A61B 5/150854 381/365 |
| 2015/0153477 A1* | | 6/2015 | Wikelski ................ G01V 1/008 702/3 |
| 2015/0209510 A1* | | 7/2015 | Burkholz ........... A61B 5/15003 604/506 |
| 2015/0379370 A1* | | 12/2015 | Clifton ................. A61B 5/0075 382/128 |
| 2016/0007567 A1* | | 1/2016 | Decaluwe ............ A01K 11/003 600/564 |
| 2016/0066916 A1* | | 3/2016 | Overmyer ................. G06F 1/30 227/176.1 |
| 2016/0116380 A1* | | 4/2016 | Bladen ..................... A61D 1/00 600/567 |
| 2016/0135433 A1* | | 5/2016 | Harty ................... A01K 11/006 600/595 |
| 2016/0157719 A1* | | 6/2016 | Spector .................. A61B 90/98 340/870.07 |
| 2016/0178392 A1* | | 6/2016 | Goldfain ................ G16H 40/67 702/104 |
| 2016/0192866 A1* | | 7/2016 | Norstrom ............. A61B 5/1123 434/247 |
| 2016/0235391 A1* | | 8/2016 | Gardner ............... A01K 11/003 |
| 2016/0249891 A1* | | 9/2016 | Gardner ............... A01K 11/006 600/567 |
| 2016/0367188 A1* | | 12/2016 | Malik .................... G16H 40/67 |
| 2017/0138822 A1* | | 5/2017 | Wimberger-Friedl ... G01N 1/08 |
| 2018/0283913 A1* | | 10/2018 | Chen .................... A61B 5/6833 |
| 2018/0296197 A1* | | 10/2018 | Kronstrom ........... A61B 5/0538 |

FOREIGN PATENT DOCUMENTS

| | | |
|---|---|---|
| CN | 1662802 A | 8/2005 |
| CN | 201675965 U | 12/2010 |
| CN | 202191315 U | 4/2012 |
| CN | 104739457 A | 7/2015 |
| WO | 2005050412 A2 | 6/2005 |
| WO | 2006122400 A1 | 11/2006 |
| WO | 2014/196876 | 12/2014 |
| WO | 2015/056229 | 4/2015 |

OTHER PUBLICATIONS

US Non-Final Office Action dated Mar. 31, 2021 for related U.S. Appl. No. 16/090,546 (35 pages).
Extended European Search Report dated Mar. 11, 2020 for corresponding European Application No. 17773418.3 (3 pages).
Chinese Office Action dated Jan. 26, 2021 for corresponding Chinese Application No. 2017800334837 (12 pages).

* cited by examiner

APPARATUS AND METHODS FOR SAMPLING

CROSS-REFERENCE TO RELATED APPLICATIONS

This application is a national stage filing under 35 U.S.C. § 371 of International Application No. PCT/IB2017/051841, filed Mar. 31, 2017, which claims priority to New Zealand Application No. 718586, filed Mar. 31, 2016, New Zealand Application No. 725097, filed Oct. 10, 2016, and New Zealand Application No. 725831, filed Nov. 2, 2016, the entire contents each of which are incorporated herein by reference.

FIELD OF THE INVENTION

The present invention relates to apparatus and methods for taking biological samples.

BACKGROUND TO THE INVENTION

To improve the tracking of livestock and to facilitate DNA testing, biological samples may be collected from animals. The sample is usually cut from an animal using a sampling device and is placed in a storage compartment for laboratory analysis.

For disease control and quality control, it is becoming increasingly important to be able to individually identify each animal with a unique code. This is typically achieved by tagging of livestock which has recently become compulsory in many countries worldwide. The tag, attached to the animal, e.g., to the animal's ear(s), has a unique identifier on or transmittable by the tag. These unique codes can be registered centrally, together with additional data related to the animal, farmer. Further, the unique identifier allows the sample to be unambiguously linked to the animal in question. Accordingly, in an outbreak of a disease, the source can be traced and the disease may be controlled more effectively and efficiently.

Despite the increased security resulting from the use of identification tags, there still remains the risk of error or fraud, e.g., cross-sampling fraud, where the sample from one animal is linked to the ID of another animal. This may occur during the sampling process if there are insufficient measures to prevent tampering of the samples.

Further, the sampling process is often labour intensive and prone to errors and inaccuracies, as the process typically requires logging of multiple pieces of information associated with each sample, concurrently while taking a sample.

Accordingly, it is an object of the present invention to provide: (a) sampling devices that go at least some way toward overcoming the disadvantages of known samplers (b) methods for collecting samples that go at least some way toward overcoming the disadvantages of known collecting methods; or (c) useful alternatives to known sampling devices and methods.

Where used in this specification tissue means any part of a living thing, particularly any part made up of similar cells, or any part or parts that perform a similar function. Tissue preferably refers to any form of biological sample, from plants and animals particularly, including pigs, goats, cattle, sheep, poultry, and fish. Biological samples may include for example, animal tissue such as flesh, blood, hair, fur, saliva, sweat, urine, or plant tissue such as leaves, bark, roots or wood, or any other part of a plant or animal but particularly those that are made up of similar cells, or which perform a similar function.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In a first aspect, the present invention may be said to be a system for taking and removing a sample from an animal, the system comprising
  A) a sampler comprising
    a handheld body to hold:
      i. a storage container holder adapted in use to accommodate a storage container capable of receiving and storing a biological sample (hereinafter "sample"),
      ii. a sample collecting device holder adapted in use to accommodate a sample collecting device,
      iii. a sample removing region provided between the storage container holder and the sample collecting device holder to accommodate an item from which the sample is to be taken,
      iv. an actuator adapted to drive a sample collecting device from the sample collecting device holder, (preferably through the item) to remove a sample from the item, and into a storage container (preferably a first end of the storage container), and
  B) a reader unit (preferably removably engaged to said handheld body or located during sampling proximate to said hand held body) and comprising one or more of:
    i. a sample identification reader adapted to capture identification information (hereinafter "sample information") associated with the collecting device and/or storage container,
    ii. an animal ID reader adapted to capture identification information (hereinafter "animal ID") associated with the item from which the sample is to be taken.

In a second aspect the present invention may be said to be a sampler comprising
  a handheld body to hold (and preferably holding):
    a. a storage container holder adapted in use to accommodate a storage container capable of receiving and storing a biological sample (hereinafter "sample"),
    b. a sample collecting device holder adapted in use to accommodate a sample collecting device,
    c. a sample removing region provided between the storage container holder and the sample collecting device holder to accommodate an item from which the sample is to be taken,
    d. an actuator adapted to drive a sample collecting device from the sample collecting device holder, (and preferably through the item) to remove a sample from the item, and into a storage container (preferably a first end of the storage container),
  a reader unit (preferably removably) engaged to said handheld body and comprising one or more of:

i. a sample identification reader adapted to capture identification information (hereinafter "sample information") associated with the collecting device and/or storage container, ii. an animal ID reader adapted to capture identification information (hereinafter "animal ID") associated with the item from which the sample is to be taken.

Preferably the reader unit comprises memory storage and/or can receive removable memory storage.

Preferably the memory storage can store animal ID and sample information, preferably associated with each other.

Preferably the reader unit comprises a transmitter to transmit animal ID and/or sample information to an external device.

Preferably the reader unit comprises a rechargeable power supply.

Preferably the reader unit, when in the form engageable to the sampler, comprises said storage container holder.

Preferably the reader unit, when in the form engageable to the sampler, comprises said storage container holder and said collecting device holder.

Preferably at least one of the storage container holder and the collecting device holder is/are permanently engaged to the handheld body.

Preferably, if the reader unit, when in the form engageable to the sampler, is removed, the sampler is still able to function to remove a sample for the item.

Preferably the reader unit, when in the form engageable to the sampler, is removable from said sampler and replaceable with a basic unit, the basic unit comprising:

A) at least one of
   a. said storage container holder and
   b. said collecting device holder, or
B) at least one of
   a. a like storage container holder, and
   b. a like collecting device holder.

Preferably the reader unit comprises a sample identification reader, and wherein said sample information to be read by the sample identification reader comprises one or more of a machine readable ID and an electronic ID, associated with the collecting device and/or storage container.

Preferably the reader unit comprises an animal ID reader and wherein said animal ID to be read by the animal ID reader comprises one or more of a machine readable ID and an electronic ID, associated with the item from which the sample is to be taken.

Preferably the reader unit comprises a sample identification reader and an animal ID reader,
   wherein each reader is configured to capture respective identification information via compatible EID communication (preferably RFID).

Preferably the sample reader and the tag reader utilise different frequencies for EID communication.

Preferably the sample identification reader operates at 125 kHz and the tag reader operates at 134.2 kHz.

Preferably the reader unit comprises a camera configured for one or more of:
   a) capturing sample information,
   b) capturing animal ID,
   c) obtaining supplemental data relating to one or more of:
      i) the item to be sampled,
      ii) location of sampling,
      iii) sampling procedure.

Preferably the reader unit comprises a positional tracking system.

Preferably the the reader unit comprises:
   a) a timer and/or
   b) means for obtaining and recording and/or transmitting time stamps.

Preferably the reader unit comprises an animal ID reader, and
   wherein the reader unit is configured to measure and/or record time between:
   a) capturing said animal ID and taking the sample, and/or
   b) taking the sample and capturing said animal ID.
   to compare the measured and/or recorded time against a predetermined time.

Preferably the sampler of any one of the preceding claims, wherein the or an actuator is adapted to drive a seal into or onto said the storage container (preferably via or at the first end) after said sample has been driven into the storage container, and wherein said reader unit is configured to provide a predetermined time limit between taking the sample and sealing the sample tube with said seal.

Preferably if said measured and/or recorded time exceeds the predetermined time the sampler or reader unit provides audio, visual or haptic feedback.

Preferably if said measured and/or recorded time exceeds the predetermined time the sampler or reader unit prompts the user to take a new sample.

Preferably if said measured and/or recorded time exceeds the predetermined time the sampler is deactivated by preventing said actuator(s) from being actuated.

And preferably the user is required to perform one or more authorisation steps comprising one or more of inputting user login details and capturing user credentials, and/or to restart the sampling process, in order to reactivate the sampler.

Preferably if said measured and/or recorded time exceeds the predetermined time, the sampler records a warning data tag associated with the sample, (preferably associated with said sample information and/or animal ID and stored on memory storage of said reader unit).

Preferably said predetermined time is between about 2 and 20 seconds.

Preferably said predetermined time limit is between about 1 second and 5 minutes.

Preferably said time limit is between about 5 and 10 seconds.

Preferably the reader unit comprises a tag reader,
   wherein the reader unit records a time stamp at the time when said animal ID is captured, and
   wherein the reader unit records another time stamp at the time the sample is taken.

Preferably the reader unit comprises a sample identification reader, and
   wherein the time of taking the sample corresponds to the capturing of said sample information on the collecting device as the collecting device is driven from the collecting device holder (preferably through the item) to remove the sample from the item.

Preferably the reader unit comprises a processor for controlling operation or operability of the sampler.

Preferably the reader unit comprises a user interface for receiving and/or capturing user credentials.

Preferably the reader unit comprises wireless communication means for transmitting data to one or more external devices.

Preferably the reader unit is able to wirelessly transmit data to one or more external devices.

Preferably the memory storage can store at least one of:
   A) animal ID and sample information, and
   B) GPS data, photographs, time stamps
   preferably associated with each other.

In a further aspect the present invention may be said to be a method of taking a biological sample from an item and placing the sample into a storage container using a sampler, said sampler comprising a handheld body presenting:
- a storage container holder adapted in use to accommodate a storage container for receiving the biological sample (hereinafter "sample"),
- a sample collecting device holder adapted in use to accommodate a sample collecting device,
- a sample removing region provided between the storage container holder and the collecting device holder to accommodate the item from which the sample is to be taken,
- an actuator adapted to drive the sample collecting device from the sample collecting device holder, (preferably through the item) to remove the sample from the item, and into the storage container (preferably at a first end of the storage container),
- an ID reader adapted to capture identification information (hereinafter item ID) associated with the item from which the sample is to be taken, the method comprising:
  a) supplying the sampler with a storage container and a sample collecting device at the storage container holder and sample collecting device holder respectively,
  b) driving the actuator to remove a sample from the item,
  c) capturing the item ID,
  wherein the time duration (hereinafter "sampling time duration") between steps (b) and (c) is monitored and/or the time of each of steps (b) and (c) are recorded as time stamps, regardless of whether step (b) occurs before or after step (c).

Preferably the sampler is as herein before described.

Preferable the item is an animal.

In yet a further aspect the present invention may be said to be a method of taking a sample from an item and placing the sample into a storage container using a sampler, said sampler comprising
- a handheld body presenting:
- a storage container holder adapted in use to accommodate a storage container for receiving a biological sample (hereinafter "sample"),
- a sample collecting device holder adapted in use to accommodate a sample collecting device,
- a sample removing region provided between the storage container holder and the collecting device holder to accommodate the item from which the sample is to be taken,
- an actuator adapted to drive the sample collecting device from the sample collecting device holder, (preferably through the item) to remove the sample from the item, and into the storage container (preferably at a first end of the storage container), and
- an ID reader (preferably removably engaged to the handheld body or located, during sampling, proximate to the handheld body), the ID reader adapted to capture identification information (hereinafter "item ID" eg animal ID) associated with (and preferably carried by) the item (eg the animal) from which the sample is to be taken, the method comprising:
  a) supplying the sampler with a storage container and a sample collecting device at the storage container holder and sample collecting device holder respectively,
  b) driving the actuator to remove a sample from the item,
  c) capturing the item ID,
  wherein the time duration (hereinafter "sampling time duration") between steps (b) and (c) is monitored and/or the time of each of steps (b) and (c) are recorded as time stamps, regardless of whether step (b) occurs before or after step (c).

Preferably the sampler comprises an or said actuator adapted to drive a seal into or onto the storage container after said sample has been driven into the storage container by the sample collector, wherein
(A) the time duration (herein after "seal time duration") between
  i. at least one of steps (b) and (c) and
  ii. sealing
is monitored, and/or
(B) the time of each of steps (b), (c) and sealing, are recorded as time stamps,
regardless of whether step (b) occurs before or after step (c).

Preferably the sampling time duration (and preferably recorded) is compared with a predetermined time limit.

Preferably the method further comprising providing at least one of audio, visual and haptic feedback to a user if said sampling time duration is longer than said predetermined time limit.

Preferably the method further comprising prompting the user to restart the sampling process if said sampling time duration is longer than said predetermined time limit.

Preferably the sampling time duration when step (b) occurs after step (c) is monitored such that if the sampling time duration exceeds said predetermined time limit, said driving of the actuator is prevented by said sampler.

Preferably the seal time duration is monitored such that if the seal time duration exceeds said predetermined time limit, said driving of the actuator to cause the seal to be driven into or onto the storage container is prevented.

Preferably if said sampling time duration is longer than said predetermined time limit and said sampler is deactivated by preventing said actuator(s) from being actuated, the user must perform one or more authorisation steps comprising one or more of inputting user login details and capturing user credentials, and/or to restart the sampling process, in order to reactivate the sampler.

Preferably the method further comprising recording or assigning a warning data tag associated with the sample if said sampling time duration is longer than said respective predetermined limit.

Preferably said warning data tag is associated with said animal ID. (preferably on a separate memory storage and/or on memory storage associated with said handheld body).

Preferably said warning data tag is associated with information carried by one of both of said collecting device and storage container.

Preferably the time of steps (b) and (c) taking place, are recorded as time stamps, and said recorded time stamps are associated with said sample. (preferably on a separate memory storage and/or on memory storage associated with said handheld body).

Preferably said time stamps are recorded and associated with information carried by one or both of said collecting device and storage container, preferably on a separate memory storage and/or on memory storage associated with said handheld body.

Preferably said time stamps are associated with said ID, preferably on a separate memory storage and/or on memory storage associated with said handheld body.

Preferably the method further comprising:
  capturing identification information (hereinafter "sample information") associated with the collecting device as the collecting device is driven from the collecting device holder and (preferably through the item) to remove the sample from the item, wherein the time of taking the sample corresponds to said capturing of said sample information.

Preferably the predetermined time limit against which the sampling time duration is compared is between about 2 and 20 seconds.

Preferably the predetermined time limit against which the sampling time duration is compared is between about 2 seconds and 5 minutes.

Preferably the predetermined time limit against which the sampling time duration is compared is between about 5 and 10 seconds.

Preferably the predetermined time limit against which the seal time duration is compared is between about 2 and 20 seconds.

Preferably the predetermined time limit against which the seal time duration is compared is between about 5 and 10 seconds.

In a further aspect the present invention may be said to be a sampling system comprising:
- a sampler comprising a handheld body defining a sampling region at where:
  - a. a storage container capable of receiving and storing a biological sample (hereinafter "sample") can be held (and preferably is held),
  - b. a sample collecting device can be held (and preferably is held), in a manner separated by a gap from said storage container of sufficient size to accommodate part of an item from which said sample it to be removed intermediate of said storage container and sample collecting device,
- the handheld body carrying an actuator adapted to drive the sample collecting device from one side of the gap, across the gap (preferably through or across the item) to remove the sample from the item, and into the storage container (preferably at a first end of the storage container),
- a reader unit removably engageable to said handheld body and comprising one or more of:
  - a. a sample identification reader adapted to capture identification information (hereinafter "sample information") associated with the collecting device and/or storage container,
  - b. an animal ID reader adapted to capture identification information (hereinafter "animal ID") associated with the item from which the sample is to be taken,
- wherein in a first mode of use, the sampler, with the reader unit engaged to the handheld body, presents a storage container holding region at one side of the gap at where the storage container can be held and a sample collecting device holding region where said sample collecting device can be held, and
- wherein in a second mode of use, the sampler, without the reader unit engaged to the handheld body, presents a storage container holding region at one side of the gap at where the storage container can be held and a sample collecting device holding region where said sample collecting device can be held.

In a further aspect the present invention may be said to be a sampling system comprising:
- a sampler comprising a handheld body defining a sampling region at where:
  - a. a storage container capable of receiving and storing a biological sample (hereinafter "sample") can be held (and preferably is held),
  - b. a sample collecting device can be held (and preferably is held), in a manner separated by a gap from said storage container of sufficient size to accommodate part of an item from which said sample is to be removed intermediate of said storage container and sample collecting device,
- the handheld body carrying an actuator adapted to drive the sample collecting device from one side of the gap, across the gap (preferably through or across the item) to remove the sample from the item, and into the storage container (preferably at a first end of the storage container),
- a reader unit removably engageable to said handheld body, or able to be located remote yet proximate thereto, and comprising one or more of:
  - a. a sample identification reader adapted to capture identification information (hereinafter "sample information") associated with the collecting device and/or storage container,
  - b. an item ID reader adapted to capture identification information (hereinafter "item ID") associated with the item from which the sample is to be taken,
- wherein in a first mode of use, the sampler, with the reader unit engaged to the handheld body, presents a storage container holding region at one side of the gap at where the storage container can be held and a sample collecting device holding region where said sample collecting device can be held, and
- wherein in a second mode of use, the sampler, without the reader unit engaged to the handheld body, presents a storage container holding region at one side of the gap at where the storage container can be held and a sample collecting device holding region where said sample collecting device can be held.

Preferably the storage container holding region is integrally formed with the handheld body.

Preferably the sample collecting device holding region is integrally formed with the handheld body.

Preferably the system may further comprising a basic unit removably engageable to said handheld body, wherein said basic unit is engaged with said handheld body during said second mode of use.

Preferably each said reader unit and said basic unit comprises a storage container holding region, to be presented to said handheld body during said respective modes of use.

Preferably each said reader unit and said basic unit comprises a sample collecting device holding region, to be presented to said handheld body during said respective modes of use.

Preferably during said first mode of use, said reader unit captures at least one of sample information and ID while said sample is removed.

In a further aspect the present invention may be said to be a sampler, substantially as herein described, with reference to any one or more of the drawings.

In a further aspect the present invention may be said to be a method of taking a sample from an item and placing the sample into a storage container, substantially as herein described, with reference to any one or more of the drawings.

In a further aspect the present invention may be said to be a sampling system comprising
(i) a handheld body to hold (and preferably holding):
  a. a storage container holder adapted in use to accommodate a storage container capable of receiving and storing a biological sample (hereinafter "sample"), b. a sample collecting device holder adapted in use to accommodate a sample collecting device, c. a sample removing region provided between the storage container holder and the sample collecting device holder to accommodate an item from which the sample is to be taken, d. an actuator adapted to drive a sample collecting device from the sample collecting device holder, (and preferably through the item) to remove a sample from the item, and into a storage container (preferably a first end of the storage container), (ii) a sample identification reader adapted to capture identification information (hereinafter "sample information") associated with the collecting device and/or storage container, and (iii) an item ID reader adapted to capture identification information (hereinafter "item ID") associated with the item from which the sample is to be taken, wherein the sample identification reader and the animal ID reader together or severally form part of one of said hand held body and a handheld portable electronic device.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION

The present invention relates to a sampler for obtaining biological samples from plants and animals particularly, including pigs, goats, cattle, sheep, poultry, and fish. Sampling from companion animals such as cats, dogs and horses is also envisaged. These biological samples may include for example, animal tissue, flesh, blood, hair, fur, saliva, sweat, urine. The invention relates more specifically to improvements in sampling, sample and animal correlation, meta-data collection, sample security and fraud reduction or prevention mechanisms for detecting, reducing and/or eliminating tampering of the sampling process or inadvertent errors during the sampling process.

Figure 3A:
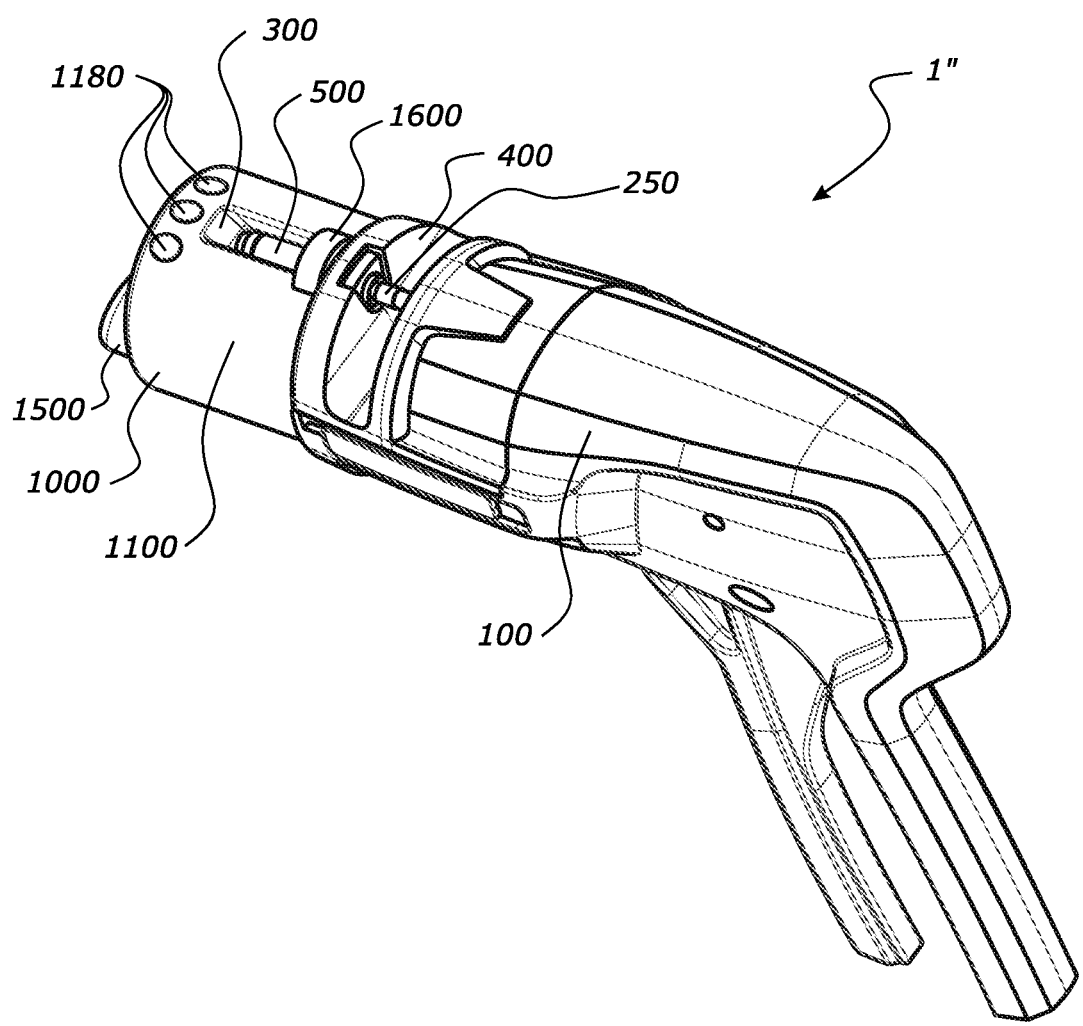
FIGS. 3a, 3b and 3c show perspective and exploded views of a sampler according to another embodiment.
Figure 3B:
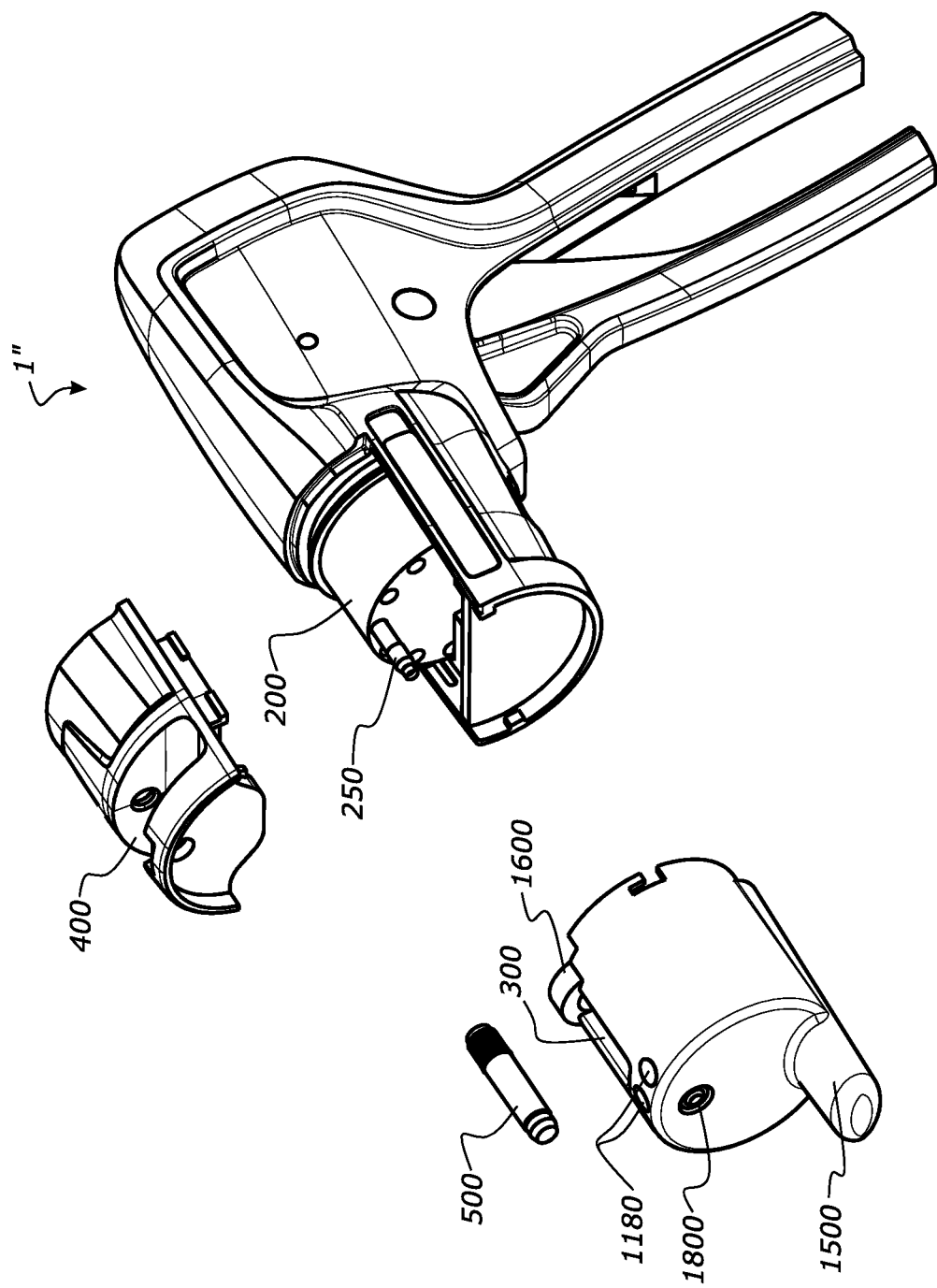
Figure 3C:
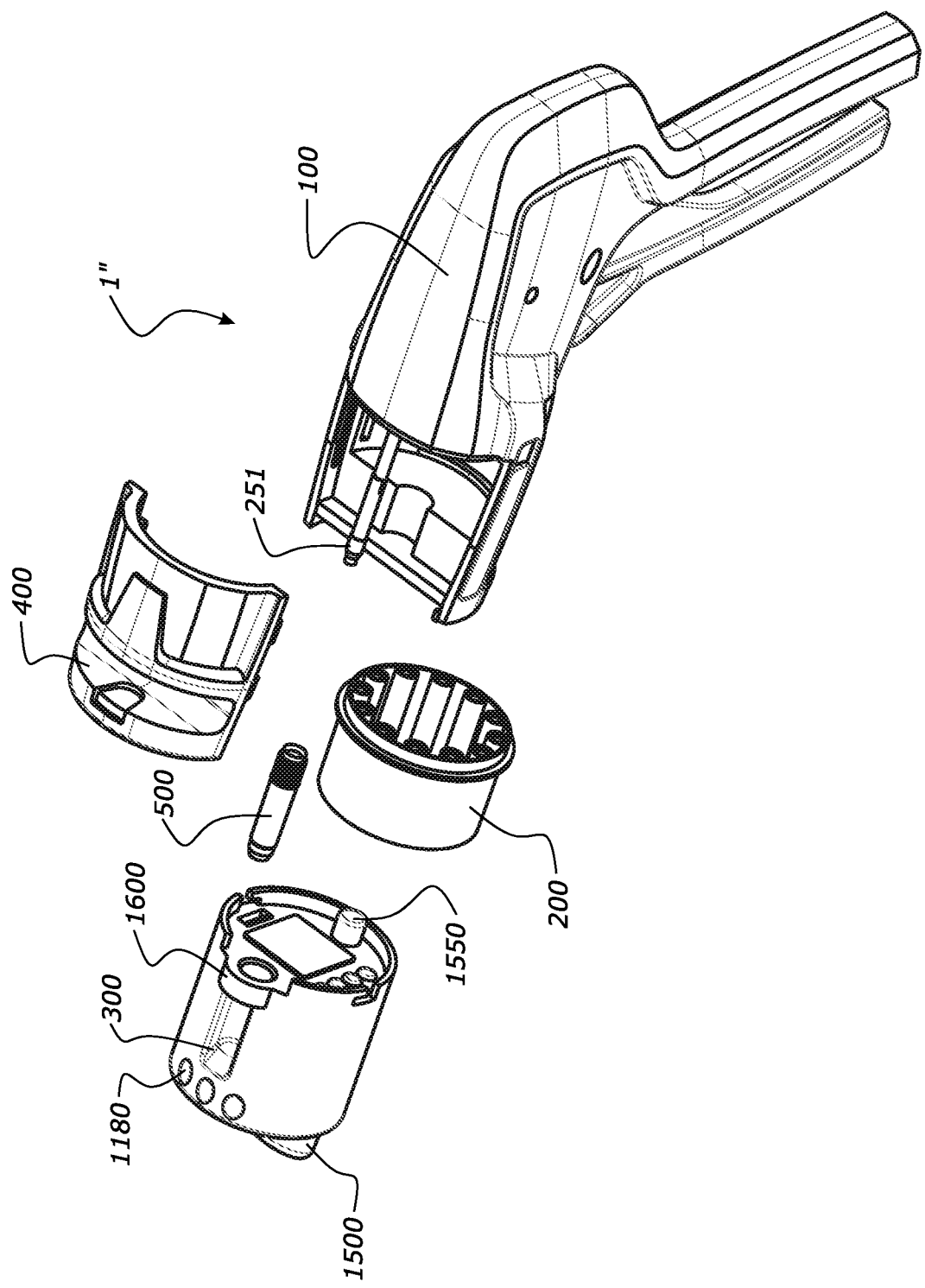
Figure 4A:
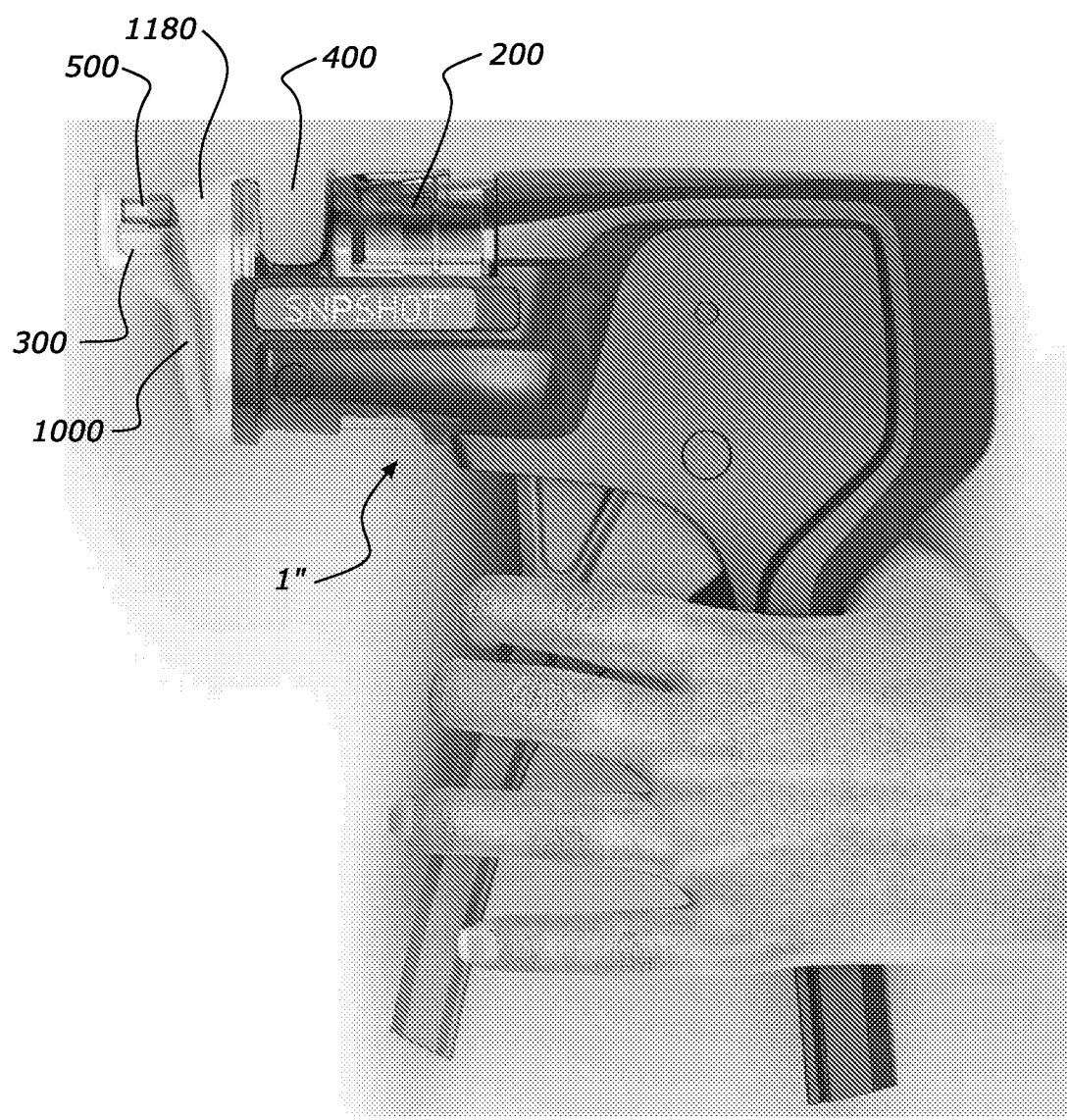
FIGS. 4a and 4b show partial and close up views of a sampler according to another embodiment.
Figure 4B:
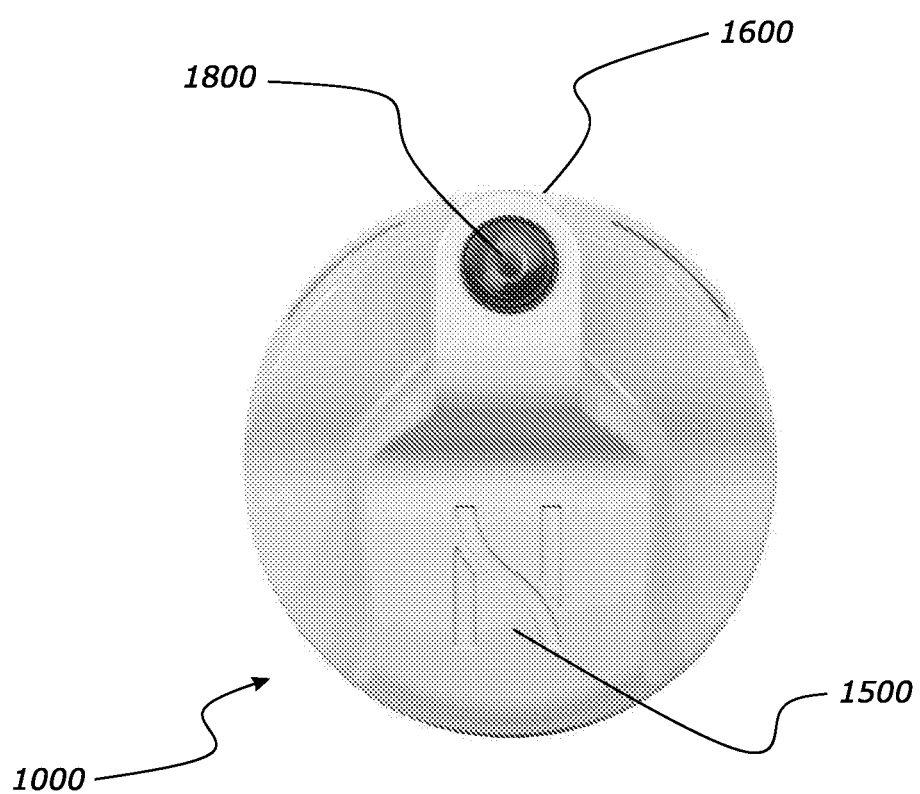

The sampler 1" as seen in FIGS. 3 and 4 may be adapted to hold a magazine comprising a plurality of collecting devices 250. Each collecting device may comprise a punch 251 having a cutting element for cutting a sample from the item (such as animal or plant material for example). Each collecting device 250 may also comprise a plunger that pushes the sample into a storage container held by the sampler by movement of an actuating means. If a magazine is included (integrally or removably) with the sampler, the magazine can be rotated, after a sample is taken, to bring another collecting device into position for taking another sample or the same or different item to be sampled, so that sequential samples can be taken efficiently.

Exemplary embodiments of the collecting device 250 that may be used with the sampler 1, 1", 1'" may be as described in patent application WO2015/056229, hereby incorporated by way of reference.

The collecting device 250 may comprise a hollow punch 251 having a cutter 255 configured to remove a sample from an organism. The collecting device 250 may also comprise a plunger 257 that is slidably movable within the punch 251, to push the sample off the cutter 255 of the punch.

Figure 2:
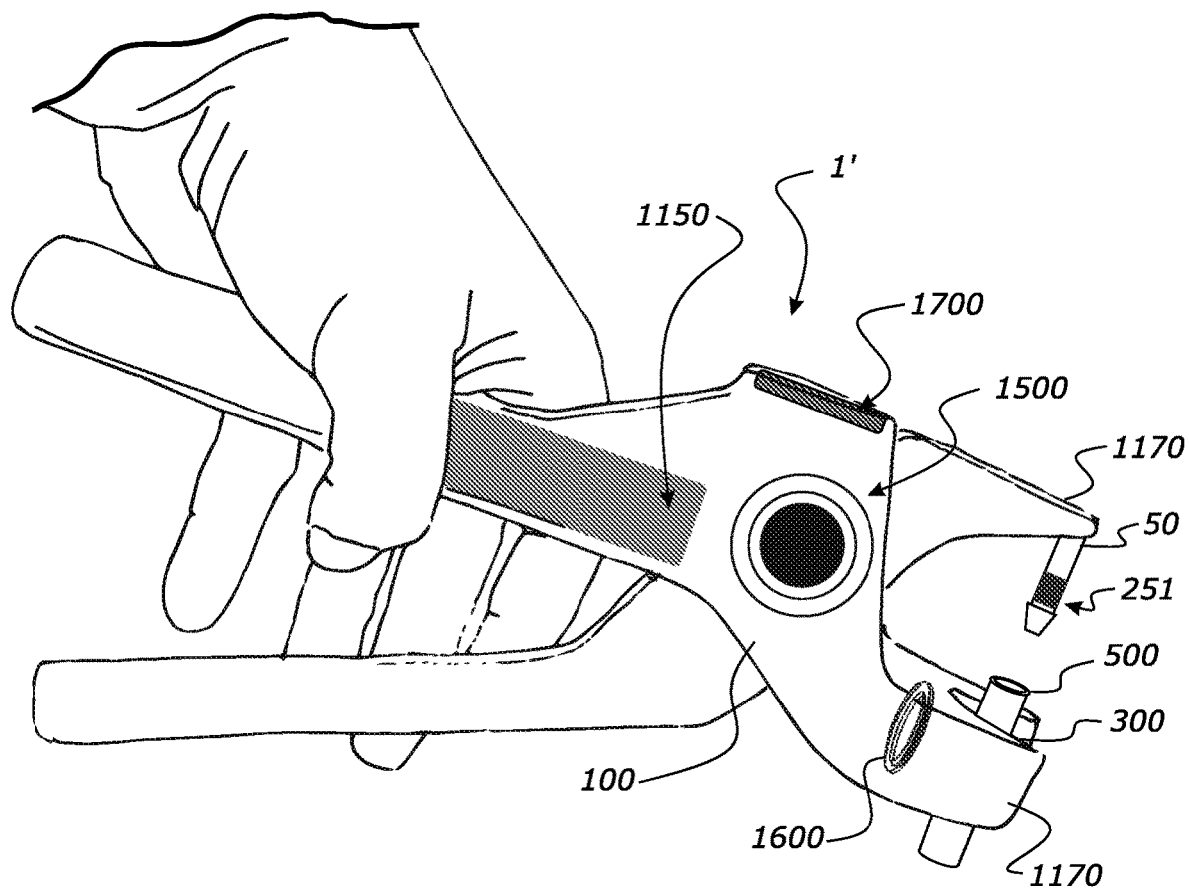
FIG. 2 is a perspective view of a sampler according to another embodiment.

In other embodiments, as shown in FIG. 2, the collecting device 250 may consist essentially of a punch 251, which is driven to punch a sample from the organism and then moved into a storage container 500.

Figure 1:
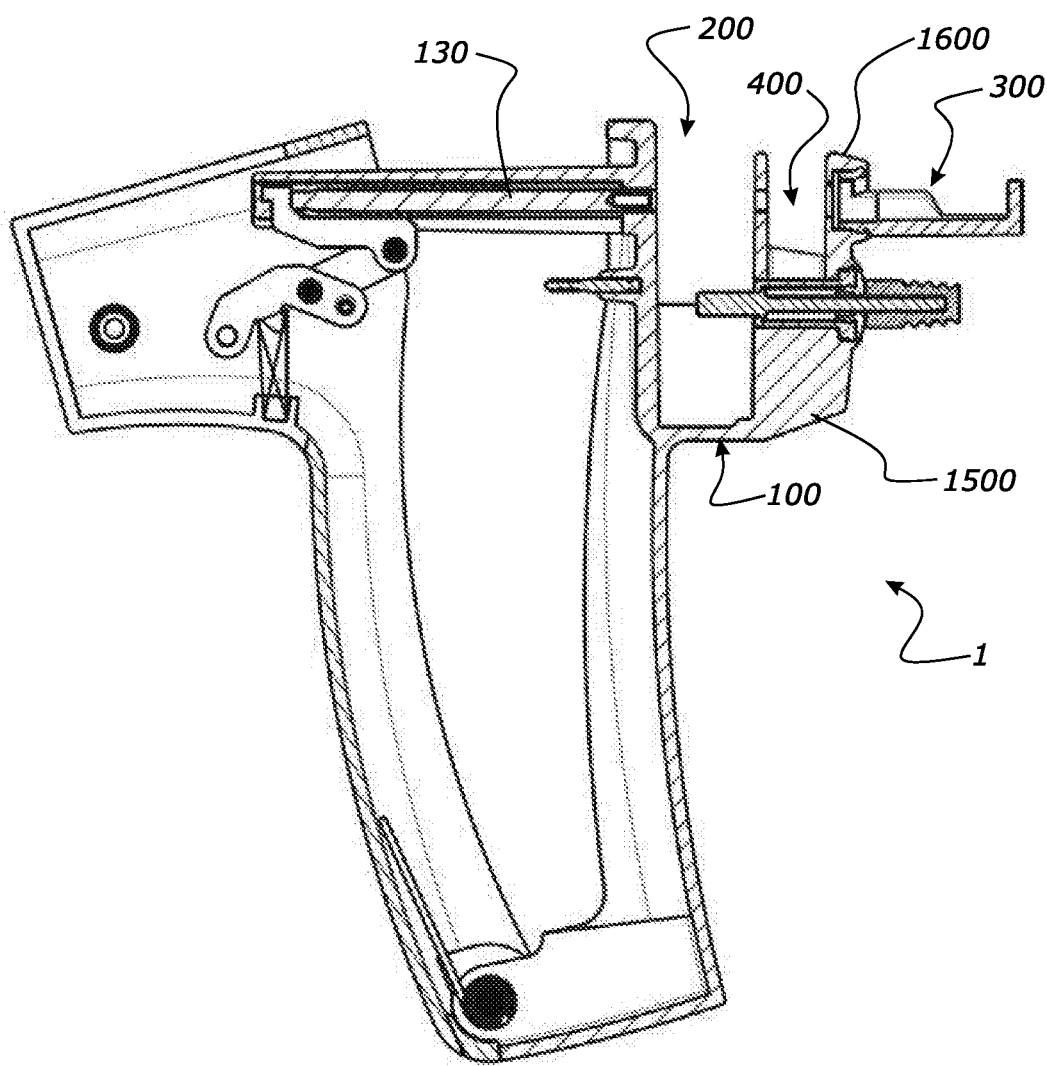
FIG. 1 is a cross-sectional view of a sampler according to one embodiment.
Figure 9:
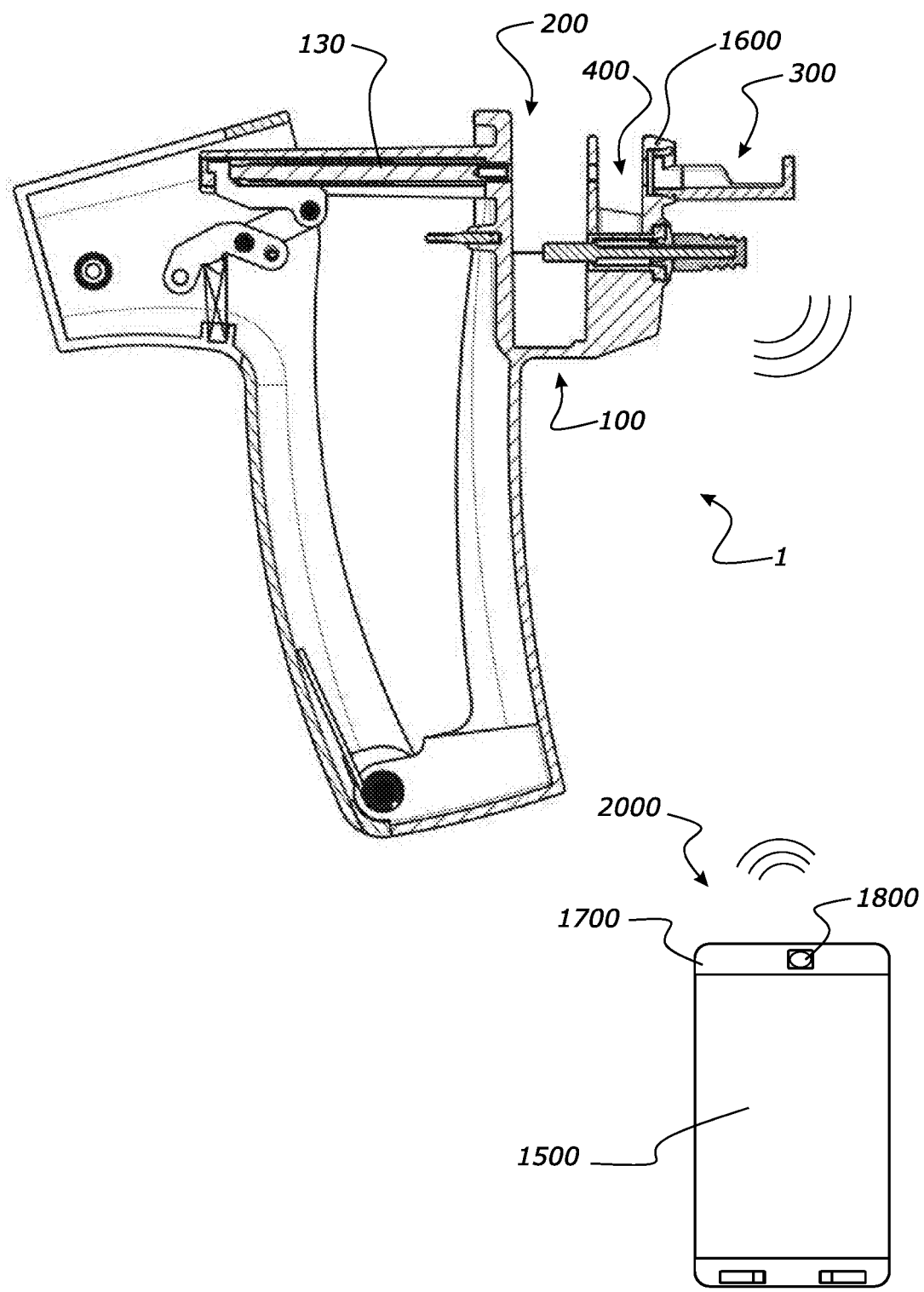
FIG. 9 illustrates a sampling system according to another embodiment.

In one embodiment as shown in FIGS. 1 and 9, and described in patent application WO2014/196876, hereby incorporated by way of reference, the sampler 1 may comprise a body 100 having a magazine receptacle 200 for holding a plurality of collecting devices 250, a storage container holder 300, and a sample removing region 400. The sample removing region is located between the magazine receptacle and storage container holder. An actuator 130 is actuable to drive the collecting device 250 from magazine 200 into storage container 300.

In another embodiment as shown in FIG. 2, the sampler 1' may comprise a body 100 having a storage container holder 300 and a punch holder 50 that may be configured to hold a single punch 251 associated with the storage container 500.

In another embodiment as shown in FIGS. 3 and 4, the sampler 1" may comprise a body 100 and a detachable scanning/sensing/reader unit 1000. In some preferred embodiments, the detachable reader unit 1000 comprises storage container holder 300 and digital memory storage 1100. In the embodiment shown, the detachable reader unit 1000 holds a single storage container 300, such that the user replaces the storage container 300 after each sample is taken. In other embodiments, the detachable reader unit 1000 may comprise a magazine for holding a plurality of storage tubes 300. For example, the magazine may be rotatable, so that new storage containers can be sequentially moved into the active collecting position for each sample.

In preferred embodiments, the body 100 of the sampler 1" comprises magazine receptacle 200 holding a plurality of collecting devices 250, and a sample removing region 400.

The sample removing region is located between the magazine receptacle and storage container holder 300.

In another embodiment as shown in FIGS. 5a to 5d, the sampler 1''' may be configured to removably receive (e.g., via snap fit or push fit or other fit) a cassette 303. The cassette preferably carries a collecting device 250 such as one described above, a storage container 300 such as one described above, and (optionally) a seal or cover 260.

Seal 260 may be provided to cover the open end of the storage container 500 once the sample has been deposited within, for additional protection of the sample against contamination. In some embodiments, where the collecting device 250 comprises a plunger 257 (that is slidably movable within the punch 251, to push the sample off the cutter 255 of the punch), the seal 260 may also be adapted to push onto the plunger when the seal engages onto the storage container 500, to thus push the sample off the punch into the storage container.

In the preferred form the cassette 303 comprises a storage container holding region 306 and a collecting device region 307. The two regions are preferably integrally connected, with a sample removing region 400 defined therebetween.

The collecting device region 307 is configured to hold the collecting device 250 and seal 260 (if provided). If the seal 260 if provided separately from the collecting device 250, the two elements may be provided by way of a collecting device and seal magazine 309, as shown in FIGS. 5a to 5d. The magazine 309 can move or be caused to move relative to the collecting device region 307 so as to selectively and sequentially present inline, the collecting device 250 and the seal 260 for actuation by the sampler 1'''.

Figure 5A:
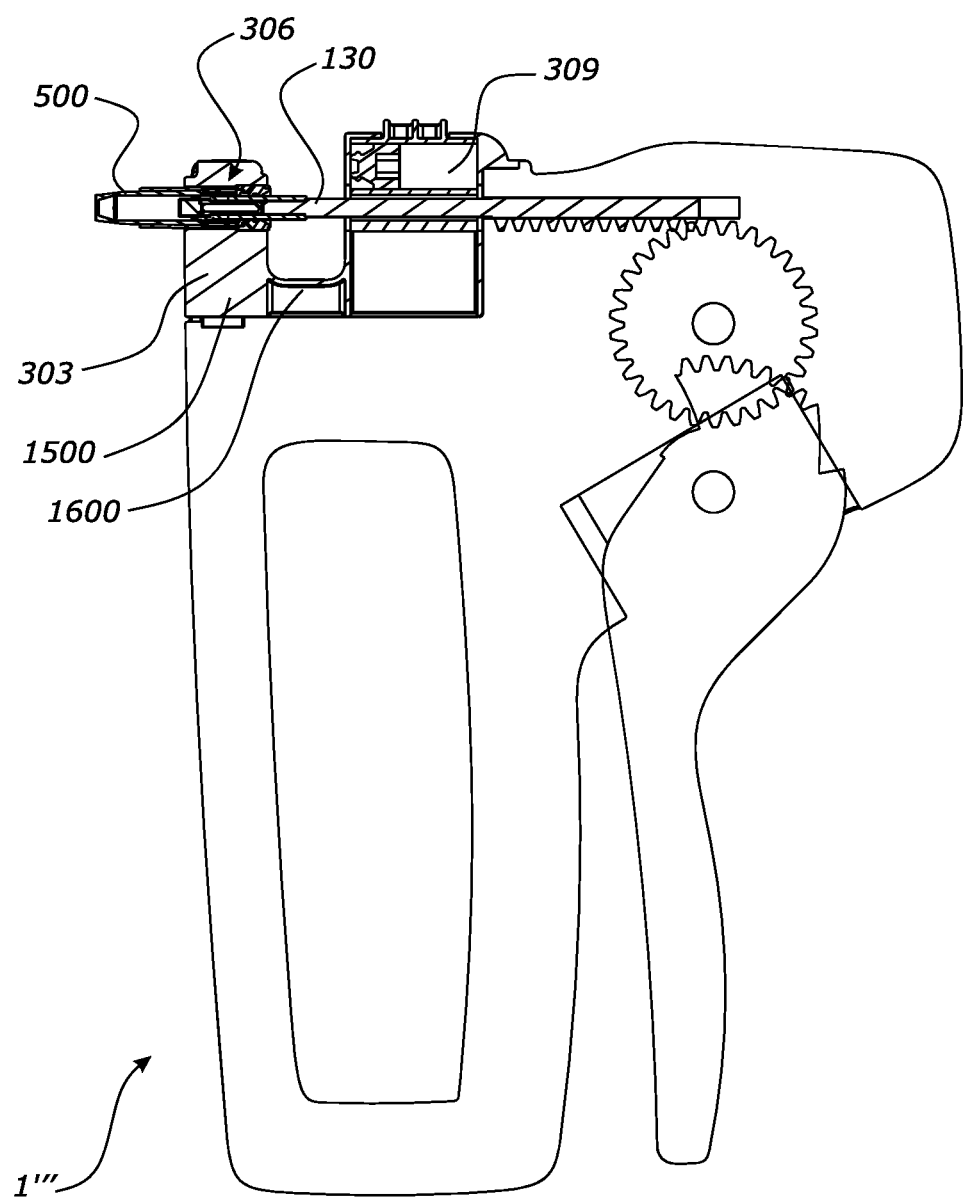
FIGS. 5a to 5d illustrate a sampling system according to another embodiment.
Figure 5B:
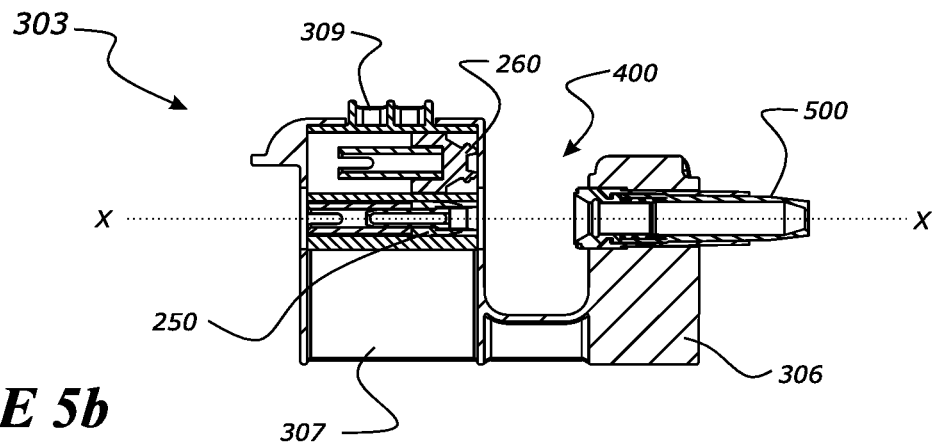
Figure 5C:
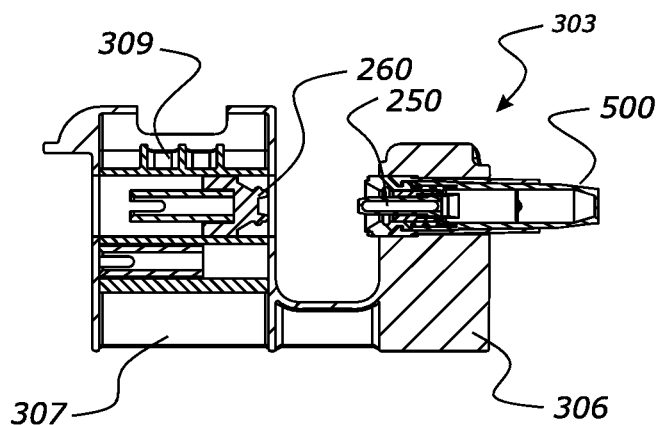
Figure 5D:
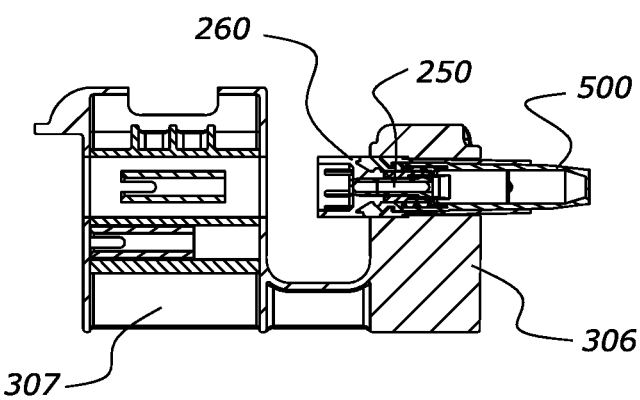

For example, FIG. 5b shows the collecting device 250 axially aligned with the storage container 500. The sampler 1''' may then be actuated to punch a sample from the organism and move the sample into a storage container 500. Subsequently, FIG. 5c illustrates the cassette 303 in a manner where the collecting device 250 has been delivered to the storage container 500, and the magazine 309 has been displaced to axially align the seal 260 with the storage container 500. The sampler 1''' may then be actuated to drive the seal 260 into or onto the open end of storage container, as shown in FIG. 5d. In some embodiments, sampler 1''' may comprise a drive mechanism that moves the actuator 130 back towards an initial/retracted position after it has been actuated, so that first the collecting device 250, then the seal 260 can be driven into the storage container in a 2-step process.

In other embodiments, where the seal 260 is not provided, or is provided integral (or in line) with the collecting device 250, a magazine may not be provided, and the collecting device region may be configured to hold the collecting device 250 (or collecting device with integral seal 260).

The cassette 303 may in some embodiments retain the storage container 500 after the sample has been taken, and the single-use cassette assembly may be shipped to a laboratory. In other embodiments, the filled storage container 500 may be removed from the cassette and shipped to the laboratory, and the single-use cassette 303 disposed. In yet other embodiments, after a sample is taken, a new storage container 500 and collecting device 250 and seal 260 (where provided) or magazine 309 (where provided) may be inserted into the cassette 303, ready for a new sample.

It should be understood that the improvements of the present invention may be applied to various forms and configurations of collecting devices and samplers (and associated methods of sampling) without departing from the scope of the invention. The present improvements add sensing, processing and connectivity components to the sampling device and process, to improve the efficiency and security of the sampling process, and are not restricted to any particular configuration of sampler.

Suitable methods of actuating the sampler to obtain a sample may be as described in WO2014/196876, incorporated by way of reference, and illustrated in FIG. 1. The magazine 200 is rotatable within sampler 1, so that unused collecting devices 250 can be sequentially moved into the active collecting position. The sampler 1 comprises actuating means to actuate, e.g., a ram, to push the active collecting device out of the chamber of the magazine 200, through the sample removing region 400 and toward the storage container. As the ram pushes the collecting device 250 through the sample removing region 400, the cutting end of the punch pushes through the item (e.g., ear or other part of the animal) to cut a sample plug from the item. The ram may be actuated via a handle or trigger of the sampler.

Any of these exemplary samplers 1, 1', 1", 1''' may comprise additional sensing, processing and connectivity components to improve the ease, efficiency, convenience, security and/or accuracy of the sampling process and subsequent downstream sample analysis.

In one embodiment, the sampler 1, 1', 1", 1''' as seen in FIGS. 1 to 4 may comprise a tag reader 1500 configured to scan or read an identifier on an animal tag that is associated with the animal from which the sample is to be taken/has been taken.

Animal tags are known in the art and have been widely used to provide a unique identification of each animal. The animal tag may comprise a human readable identification component, such as an alphanumerical sequence printed or otherwise provided on the animal tag. The animal tag may additionally or alternatively comprise a visible machine readable component such as a linear barcode or a matrix barcode such as quick response (QR) codes. The animal tag may additionally or alternatively be an electronic identification (EID) tag, e.g., a radio-frequency identification (RFID) tag, a near field communication (NFC) tag, which comprises electronically stored information and means for transmitting this information to the tag reader. In some cases, the animal tag may be embedded (e.g., subcutaneously) in the animal; in other cases, the tag is attached to the animal (e.g., to the animal's ear) such that at least a portion of the tag is visible to the user; in yet other cases, the tag is marked onto the animal, e.g., via branding, tattooing.

Where RFID is used, the RFID system may operate in a suitable frequency range, e.g., low frequency (LF), high frequency (HF), ultra high frequency (UHF). The frequency range may be selected according to effectiveness over the distances required, according to regulation or standards, and/or so as not to interfere with other RFID systems (as discussed in more detail below).

The tag reader 1500 is accordingly configured to read, sense, scan, capture and/or record one or more identification components from the animal tag. In some embodiments, the animal tag reader 1500 is configured to be able to capture identifiers from more than one type of animal tag, for greater versatility across a range of different environments and scenarios.

In one embodiment, the tag reader 1500 is configured to read electronically stored data from an EID tag. For example, the animal tag may comprise a passive RFID transponder that is powered inductively by the animal tag reader. Alternatively, the animal tag may be an active RFID tag. The tag reader 1500 comprises an RFID reader antenna configured to read the electronic ID transmitted by the animal tag across a specific carrier frequency or frequency band.

Preferably, the configuration of the RFID system conforms to ISO standards 11784 and 11785. Accordingly, the RFID system is preferably a low frequency (LF) system, and operates across the ISO-compliant carrier frequency of 134.2 kHz. However, it will be appreciated that the RFID system could be instead compliant with other national or regional standards relating to animal identification and tracing, and may therefore operate at or across other frequencies as appropriate.

The tag reader 1500 may additionally or alternatively comprise a barcode or QR code scanner for use with tags that have no RFID capability. In these cases, the tag reader 1500 may comprise a barcode scanner, image scanner, a camera or other image capturing means. The tag reader 1500 of sampler 1, 1', 1", 1''' may further comprise a processor running image recognition software for processing and interpreting the captured barcode image. In other embodiments, the tag reader 1500 may simply record the barcode image, to be transferred to a separate storage location, apparatus, database, server, for subsequent processing and interpreting.

Additionally or alternatively, the tag reader 1500 may be a camera 1800 for recording human viewable/readable animal ID or ID components, such as alphanumeric serial numbers, from the animal tag. Similarly, the recorded image may be processed using image recognition and processing software, whether this is run on board the sampler, or after the data has been transferred to a remote server.

Further, the camera 1800 could also be used to take photographs or videos of identifying features of the animal, for example, photographs of the animal tag, biometric data such as a retinal scan of the animal, visual patterns on the animal such as colouring variation or distribution of spots, or other identification features such as visual brands on the animal, ear notches. This biometric identification data may be captured in addition to, or instead of, identification from an animal tag associated with the animal.

The camera 1800 may be provided with one or more accessories (whether integrally formed with the camera or not) such as a flash, laser pointers, for use in low-light conditions and/or as a laser "sight" to increase accuracy of focus on the ID component or other identifying features of the animal before/when capturing the photograph. Other accessories may include rangefinders (e.g., laser rangefinders), proximity sensors, infrared sensors, to aid with focusing and capturing of photographs and optionally also to obtain more information about the images captured e.g., distance.

The user may be prompted to scan the animal tag and/or capture other animal identification data immediately before and/or immediately after taking the sample of the animal. This prompting may be by way of visual, audio or haptic feedback. For example, a countdown timer may be visible and/or audible.

Timing between the scanning and sampling steps may be restricted, regulated, recorded or monitored, as discussed in more detail below. In other embodiments, the scanning or transmission of the animal EID may be automatically activated, for example, actuating the trigger of the sampler to take the sample may simultaneously activate the tag reader 1500 to read the EID and/or capture the image.

In preferred embodiments, the sampler is configured to so that there is a predetermined time limit between (1) scanning or reading of the animal ID and (b) taking the sample or taking of a sample marked as valid (eg a validated sample) and that accordingly will or should be treated as valid in subsequent processing, (or vice versa). This can help reduce the risk of cross-sampling fraud (i.e., prevents the user from scanning one animal's tag and taking a sample from another animal). For example, the user may be provided with between three seconds and ten seconds after scanning the animal tag to complete the sample taking process. This time limit may be factory set. This time limit may be programmable by an authorised user, so that it may be adapted for different scenarios.

In some embodiments, if the sample is not taken within the time limit, the user may be notified (via sound, visual, haptic feedback) and the user will need to rescan the animal tag before the sample (or a validated sample) can be taken. That is, the sampler may be blocked or deactivated such that the punch of the collecting device cannot be actuated unless the animal tag is rescanned.

In some embodiments, if the sample is not taken within the time limit, the sampler may be deactivated, e.g., the actuator 130 may be prevented from being actuated (for example via solenoid pins that lock the push rod), the sampler may power off or go into standby mode, until the user performs one or more authorisation steps, e.g., by inputting user login details (may be user's login details or a supervisor's login details), or by capturing user (or a supervisor's) credentials e.g., sensing, reading, and/or recognising one or more identifiers associated with the user, such as a barcode, QR code, EID on a user's ID card, and/or biometric data such as the user's thumbprint, eye scan. Further, the user may also be required to restart the sampling process once the authorisation step(s) have been performed, in order to reactivate the sampler.

In other embodiments, if the sample is not taken within the time limit, a data warning tag is added to the data associated with the sample, so that a laboratory analyst will be aware that the time limit was breached during that particular sampling instance. Ie the sample is not valid or is not a validated sample. Exemplary embodiments for associating data with the sample, e.g., via an ID on the collecting device or storage container, are described in more detail below.

Alternatively, instead of setting a predetermined time limit or timer, the sampler could record two time stamps, one at the time the animal tag is scanned, and another at the time the sample is taken. The duration between the two time stamps may then be assessed, e.g., at the laboratory, to determine if too much time elapsed between these two events. The sample may then be treated as non-validated sample.

Preferably, the identification of these events (i.e., capturing the animal ID and taking the sample) is performed automatically by the sampler or associated portable device, and cannot be modified by the user. For example, a proximity or magnetic switch 1550 may be provided in a suitable location to confirm that the collecting device 250 or punch 251 has moved, e.g., out of magazine 200, or into storage container 500. This automatic detection can therefore be linked unambiguously to the sampling action.

It will be appreciated that other means of detecting the sampling action may also be suitable, e.g., as will be discussed in more detail below, the sample ID reader may be positioned to only capture the ID of the actual collecting device while it is moving to take a sample or after it has moved into the storage container after taking a sample.

Accordingly, the time of the reading of the sample ID could be used as an unambiguous confirmation of the sampling action.

The required scanning process may either require the animal identification data to be captured before or after taking the sample. Where the scan is done after taking the sample, the procedure would not prohibit a sample from being taken (e.g., by deactivating the sampler) if the time limit is breached, but the sample could be tagged with data warning tags as described above.

For extra security, a multi-scan process may be implemented. For example, the user may be required to scan the animal tag, take the sample, then re-scan the animal tag. Optionally, this must all be done within a predetermined time period. This will help to reduce the risk of cross-sampling fraud.

In one embodiment, the animal tag reader 1500 may be provided integrally with (and permanently attached to) the sampler, as shown in FIGS. 1 and 2.

In another embodiment, the animal tag reader 1500 may be provided on a reader unit 1000 that is removably attachable to the body 100 of the sampler, as shown in FIGS. 3 and 4. In this embodiment, the detachable reader unit 1000 may also comprise inbuilt memory storage 1100 and/or means for receiving removable memory storage, e.g., memory cards, USB, for storing the animal ID. The animal ID data and other data such as time stamp data may be written to the memory storage to be recorded thereon. Alternatively, the reader unit 1000 may transmit the animal ID and other data to an external device or database without storing the data on the reader unit 1000.

The detachable reader unit 1000 may be configured to be reversibly attached to the sampler via any suitable attachment means, e.g., snap-fit, interference fit, screw-fit, a lug and slot connection (as shown in FIGS. 3*a* to 3*c*), clamps.

In a third embodiment, the animal tag reader 1500 may be physically separate from the sampler. For example, as shown in FIG. 9, the animal tag reader 1500 may comprise a smartphone 2000 or other portable computing device, having a camera which may function as a barcode/QR code scanner, and/or having RFID/NFC capabilities for receiving EID data from the animal tag.

The smartphone 2000 may run software or applications to provide a user interface to facilitate the link between the smartphone and the sampler. Additionally, the smartphone 2000 may perform some or all of the image recognition and processing of the captured data. Alternatively, some or all of the raw captured data may individually or collectively be transmitted (whether via a wired or wireless connection) to a server or database for further processing.

In preferred embodiments, the sampler may be wirelessly connectable to a smartphone 2000 via, for example, Bluetooth, Bluetooth low energy (BLE), Wi-Fi, infrared, NFC, mobile networks such as GSM, GPRS, 3G, 4G LTE, to perform one or more of the following functions: user authorisation, data transfer, user interaction. Further, even for the embodiments where the animal tag reader 1500 is provided on the sampler, the sampler is preferably able to connect wirelessly with a smartphone or other portable computing device to facilitate one or more of these functions.

In alternative embodiments, the sampler may comprise a holder or other means for temporarily attaching a smartphone 2000 or other portable computing device to the body 100 of the sampler. In addition to physically mounting the smartphone 2000 to the sampler, some embodiments may provide means for wired data connectivity between the two devices (for example, a USB plug connection) while the smartphone 2000 is mounted to the sampler.

In preferred embodiments, the sampler 1, 1', 1", 1''' also comprises a sample ID reader 1600 to read, sense, scan, capture and/or record one or more identification components of the collecting device 250 and/or storage container 500.

For example, the plunger 257 or punch 251 of the collecting device 250 may comprise a machine readable EID tag, such as an RFID tag. The RFID system may be selected according to the anticipated manufacturing and use conditions of the sample collector. For example a typical passive tag, active reader system operating at low frequency can provide robust identification devices suitable for embedding in molded plastic components at a unit cost that is appropriate. Other systems, such as NFC, or passive or active tag systems operating in the high frequency (HF) or ultra high frequency (UHF) range may also provide affordable, effective solutions.

If the sample ID is transmitted via RF, the electronic ID transmitted by the tag on the collecting device 250 or storage container 500 is preferably across a carrier frequency that is different from the carrier frequency of the animal tag ID (if an RFID animal tag is used or intended to be used). For example, the sample ID tag preferably does not operate over 134.2 kHz, which is the ISO-compliant frequency for the animal EID. This will ensure that the two tagging systems do not interfere with each other. In one example, the sample ID system operates at 125 kHz.

The sample ID reader 1600 may be integrated to the sampler, or mounted to the sampler, adjacent the position that the sample, the collecting device 250 or the storage container 500 occupies before or after the sample has been taken, and/or adjacent the position that the collecting device 250 passes through while taking the sample. Examples of suitable locations of the sample ID reader 1600 are shown in FIGS. 1 to 4 respectively.

In the example of FIGS. 3 and 4, the sample ID reader 1600 may be located on the detachable reader unit 1000, adjacent where the collecting device 250 moves into the storage container 5000 when the sample is taken.

Preferably, if a magazine 200 of collecting devices/punches is provided, the device has means for selectively reading only the ID of the actual collecting device 250 or punch 251 that is currently being used to take the sample. For example, the other collecting devices/punches may be shielded from being scanned by the sample ID reader 1600, e.g., by manufacturing (at least part of) the magazine from an RFID blocking material, Faraday's cage.

In another example, the sample ID reader may be tuned to very close range, such that it only reads a collecting device 250 or punch 251 that is directly adjacent to it (this being the collecting device/punch that has been moved into position, ready for use).

In another example, the sample ID reader is located away from the pre-use position of the collecting devices/punches, and positioned adjacent where the collecting device 250 or punch 251 will pass through while taking the sample, or where the collecting device 250 will end up after taking the sample. One advantage of this embodiment is that this provides a means for automatically and unambiguously detecting the sampling action. The exact time of the sampling action may therefore be linked to the time that the sample ID reader captures the sample ID, and this data may be used to implement the restricted time limit between capturing the animal ID and taking the sample, as described above.

In cases where the sample ID is not an electronic ID, e.g., it may be a barcode, QR code, the sample ID reader is configured to scan/read the sample ID as appropriate, e.g., the sample ID reader may be a camera, barcode scanner, smartphone with camera.

In some embodiments, the sampler may comprise GPS or other 3D positional recording or tracking systems for providing location data. Additionally or alternatively, the sampler may also comprise other forms of positioning technology to provide location data, including but not limited to cell phone network based triangulation, Wi-Fi-based geolocation by the correlation of the SSID, MAC address or other identifiers of the Wi-Fi access point with a public or private database of locations associated with the Wi-Fi access point.

Where Wi-Fi geolocation is used, this form of positional information may be supplemented with one or more other commonly used localisation techniques. Such techniques may include the estimation of position based on signal strength from one or more access points, fingerprinting, angle of arrival based techniques where more than one antenna or access point is available, or time of flight techniques.

For example, the sampler may comprise a GPS or other positioning technology module 1700 to obtain or estimate the location where a sample was taken. The positioning technology module may be provided either as a component either separate and preferably connectable or associable with the handheld body of the sampler, or may be integral with the handheld body of the sampler. Where provided separate from the handheld body, the positioning technology module 1700 may be provided by the smart phone 2000, where present. It is contemplated that the positioning technology module 1700 may additionally be provided by any other commonly available device capable of In the case where the positioning technology module 1700 is provided by the smart phone 2000, the smart phone may be located near to the sampler, such that the location data may be transmitted to the sampler. In order to prevent fraud by the recording of location data not sufficiently close to the actual location of the sampling, it may be preferable to limit the range within which the smart phone 2000 may communicate with the sampler. Such a range limitation may be provided by using short-distance communication protocol, such as Bluetooth or Wi-Fi. Alternatively, it may be provided by requiring a wired connection between the sampler and smart phone. In these cases, the smart phone may be carried by the user while sampling, or may be located nearby such as on a fence post, in a nearby vehicle.

Additional security measures may optionally be employed, e.g., back-up position tracking systems, additional cell tower metadata, assisted GPS, to prevent GPS spoofing fraud, verify the collected location data, and/or increase accuracy of the location data.

In the preferred form is contemplated that the accuracy of location data is desired to be such that it is possible to distinguish between farms or regions within farms, or individual ocean areas, but not necessarily to the level of individual animals or plants. However, in alternative forms more accurate location data may be able to be provided, such that it is possible to determine between specific areas of land or sea.

The location data may then be recorded and linked to the sample (e.g. sample ID, animal ID, other relevant information associated with the particular sample). This linking of the data may be performed onboard the sampler, via a connected device such as a smartphone 2000, and/or after the datasets have been transferred to a server or database.

Where the location data is linked to the sample it may be desirable, in order to prevent fraud, to provide a time limit between the sample being taken and the sampler acquiring the location data from the positioning technology module 1700. If the time between the sample being taken and the acquiring of the location data exceeds the time limit, the sampler may either reject the sample or record this information for assessment at the laboratory. This may go at least some way in preventing fraud by sampling of an animal in a first location, but the provision of location information from a second location.

In addition to measuring a time between sampling and the provision of the location information from the positioning technology module 1700 the sampler may require that the location data be timestamped within a particular time period. This may further prevent the spoofing of positioning information and the recording by the sampler of inaccurate location data.

At the laboratory the time timestamps and locations of each recorded sample location may be compared against the time between each related sample, in order to determine if the distances travelled between each successive sampling was possible in that amount of time. Where this analysis is conducted, some leeway may be provided dependent on the accuracy and type of positioning technology that is utilised.

In addition to the location data, other information such as time and date, images of the sample location, may be captured immediately before, during or immediately after the sample is taken, and the data linked with each other to provide a comprehensive collection of data tags associated with a particular sample. For example, actuating the trigger of the sampler to take the sample may simultaneously initiate the recording of these additional data.

Increasing the number and variety of data tags associated with a particular sample will generally increase the security of the sampling process, sample tracking and sample processing. Further, automating the collection of these data will reduce labour costs by eliminating or reducing steps which may previously have been done manually, such as writing down the date and time as each sample is taken.

Location data or other information, as described above, that is captured and associated with a particular sample may be stored on the sample tube 500, or may be recorded on the sampler itself, or on a connected device such as a smartphone 2000, where present. Recorded data on the sampler or connected device may be instantaneously uploaded to a desired location for review at the laboratory, or may be manually uploaded, such as by reading the data off a memory card associated with the sampler, at a later time.

Where location data or other information is associated with a sample and stored or transmitted, it may first be encrypted by either the sampler or associated connected device prior to storage or transmission. This encryption may assist in preventing fraudulent modification of the data, such as by the insertion of a falsified data stream. The information required for decrypting the data may be provided at an authorised end source, such as a laboratory where the samples are reviewed.

An additional layer of security may be provided by requiring operator authentication prior to using the sampler, and/or prior to taking a sample. Operator login may be performed via direct operator input to the sampler, via switches, touch screens, keypads, provided on the sampler. Alternatively, the operator may instead log in via an application on a connected device such as a smartphone 2000.

Alternatively, instead of operator input, the user's credentials may be obtained by sensing, reading, and/or recognising one or more identifiers associated with the user, such as a barcode, QR code, EID on a user's ID card, and/or biometric data such as the user's thumbprint, eye scan.

For particularly high risk situations, the user may be prompted to input user credentials intermittently or regularly throughout the entire sampling process. Preferably, in such cases, the sampler and/or connected device may be configurable such that the frequency of the user input prompts may be varied depending on the security required for a particular situation.

The embodiments shown in FIGS. 3 and 4 illustrate one particular configuration of a sampler 1" comprising a standalone reader unit 1000, which is attachable and detachable from the sampler body 100. This reader unit 1000 preferably comprises the animal tag reader 1500, the sample ID reader 1600 and memory storage 1100. In some embodiments, the reader unit 1000 may further comprise processing system including a communication module, e.g., for wireless communication with a smartphone. The detachable reader unit 1000 may also comprise a GPS module 1700, or other position tracking components. The detachable reader unit 1000 may also comprise a camera 1800 which, in some cases, may function as animal ID reader 1500 and/or sample ID reader 1600.

Accordingly, the detachable reader unit 1000 may comprise essentially all the "smart" components of sampler 1". The reader unit 1000 may be standalone, in that it may be powered by its own battery 1900, which may be rechargeable via any known method, such as a removable rechargeable battery, USB charging, wall socket charging, inductive charging. The reader unit 1000 is preferably completely sealed and weather resistant, water resistant or waterproof.

Further, as the reader unit 1000 preferably contains its own memory storage 1100, e.g. inbuilt memory or removable memory, the reader unit 1000 may be hot swappable from the sampler while the sampler remains in operation. That is, the reader unit 1000 may be replaced with another reader unit while the sampler remains in operation. This may be done when the memory storage 1100 is full, so that the data may then be uploaded to a server or database.

While preferably provided attachable and detachable to the sampler body 100, it is contemplated that the reader unit 1000 may be provided by the on-board functions or connected functions of a smart phone 2000 where present, or may alternatively be provided as another separate element, not attachable or detachable to the sampler body 100. In the example of a smart phone 2000, the reader unit 1000 may also be able to be attached and detached to the sampler body 100, or may be provided proximate to the sampler body. For example, where the reader unit 1000 is comprised by the smart phone 2000 and/or other devices connected to it, the smart phone may be worn the user who is conducting the sampling, on the body or in their clothes.

Where the reader unit 1000 is comprised by the smart phone 2000 and/or other commonly available devices connected to it, Where the reader unit 1000 is not attachable or detachable to the sampler body 100 it may be provided proximate to the sampler such that it is still able to receive and record animal ID information from the sampler. The sampler and reader unit 1000 may communicate by any commonly used communication platforms such as RF, Wi-Fi, Bluetooth.

While not attached to the sampler body, the reader unit 1000 would preferably be sufficiently proximate to facilitate communication between the sampler and reader unit. For example, the reader unit 1000 may be located on the person of the user of the sampler, on the ground or a fence post nearby to where the sampling is taking place, or in or on a vehicle nearby.

Figure 6:
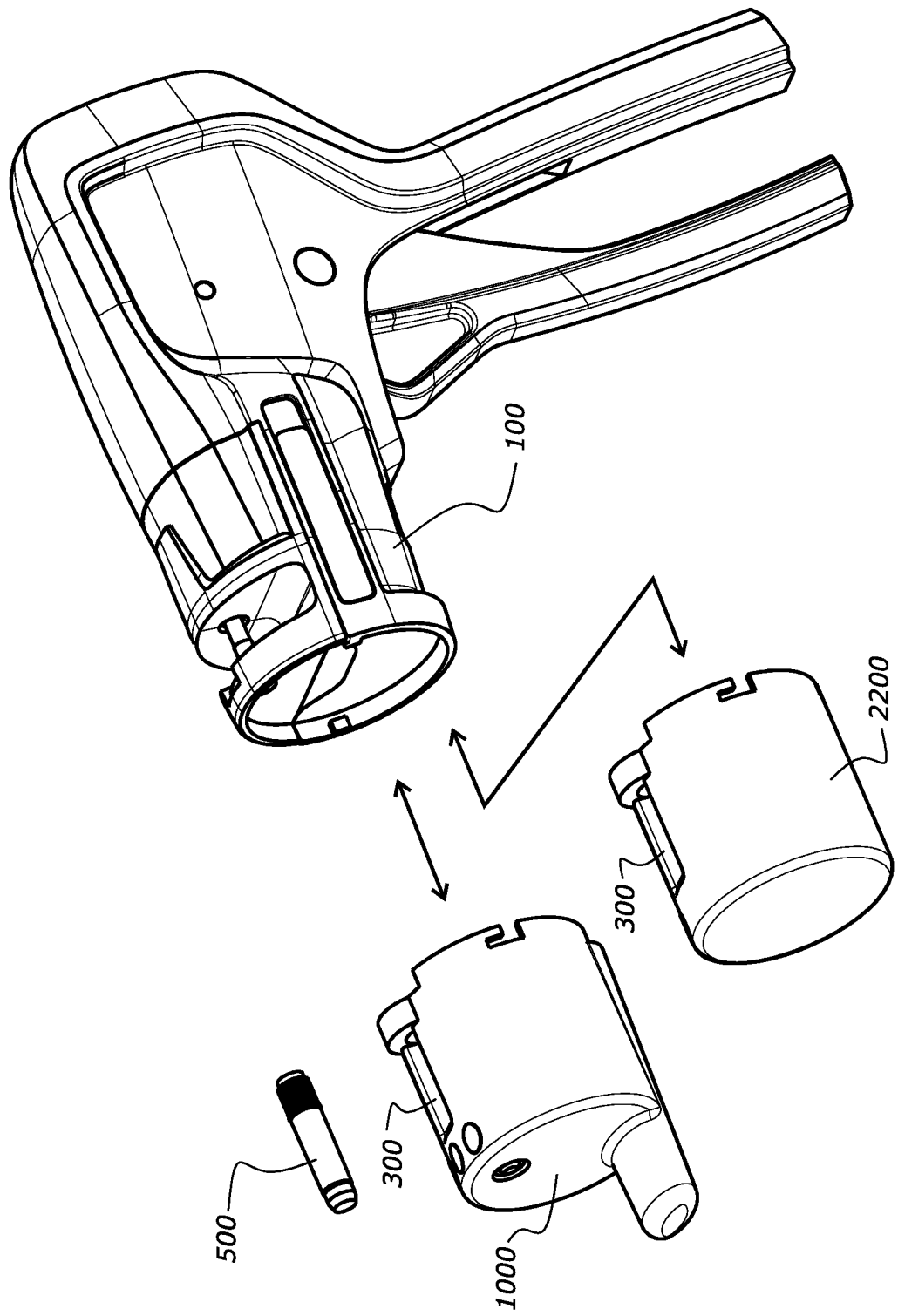
FIG. 6 shows a removable smart reader unit and replacement standard storage holder unit according to an embodiment.

In some embodiments as illustrated in FIG. 6, the standalone, hot swappable "smart" reader unit 1000 may be removed from the sampler, and the sampler used without the smart reader unit. In one example, a replacement storage container holder 2200 may be attached to the front of the sampler, so that the sampler may then operate as a basic, "non-smart" device. This "non-smart" storage container holder 2200 may comprise a holder for a single storage container 500, or may comprise a magazine for holding a plurality of storage containers 500.

This allows for increased versatility of the sampler, for adapting to different environments depending on the security risk. That is, for high risk, high security environments, the sampler may be used with the "smart" reader unit 1000 to provide an additional level of security and reduce the risk of tampering, while for lower risk environments, the reader unit 1000 may be removed (and optionally replaced with a standard sample tube holder 2200) to perform less secure, but quicker and (potentially more cost-effective) sampling. Accordingly, this provides several options for the user, i.e., a basic, low-cost system, which may be subsequently upgraded to a "smart" system if/when required.

In some embodiments, the sampler body 100 may not comprise a power supply and/or electronic components, and therefore relies on the detachable reader unit 1000 for the "smart" components of the system.

In other embodiments, the standalone, hot swappable "smart" reader unit 1000 may be configured to receive both the storage container 500 and collecting device 250. For example, the cassette 303 received by the sampler 1''' may be provided in two different forms, a "smart" cassette comprising, e.g., animal ID reader 1500 and/or sample ID reader 1600, memory storage 1100, (as illustrated in FIG. 5a) and a basic "non-smart" cassette. That is, the sampler 1''' may be configured to receive either a "smart" cassette/reader unit, or a basic "non-smart" cassette which would still allow the sampler to perform the basic sampling procedure.

Where the sampler operates as a basic, "non-smart" device, a separate smart device 2000 may be provided in order to provide at least some of the herein described smarts of the system. For example, where the smart device is capable of reading RFID tags, the smart device may be used to scan a EID tag, such as an RFID tag, on the plunger 257 or punch 251 of the collecting device 250 or the punch 251, then also taken an associated animal ID. The associated animal ID may also be in the form of an RFID tag, or may be in the form of any one or more of the other forms of animal ID herein described.

Specifically, the smart device may scan the RFID tag of a collecting device 250 or punch 251, then also take a location data point from the on-board positioning systems of the smart phone. These pieces of information may then be associated with each other and stored on the smart device, for later transfer or analysis.

Any one or more other forms of animal ID may also be taken simultaneously, or preferably within a predetermined time period. For example, the user may take a photograph of the animal using the smart device 2000. Where additional animal ID is to be provided by the user, a maximum time threshold after sampling, or after the scanning of the collecting device or punch, may be required in order for the animal ID to be validly recorded. As herein described, if the time threshold is not met then the smart device 2000 may reject the sample and require re-sampling, or may record the fact that the threshold was surpassed along with the other animal ID information.

In order to prevent fraud, and ensure that the collecting device 250 or punch 251 which are scanned by the smart device are associated with the correct sample, either or both of the smart device and sampler may be configured such that the collecting device 250 or punch 251 may only be scanned during the sampling process. Such a configuration may involve shielding of the collecting device or punch prior to sampling, or a particular location of the smart device 2000 in relation to the sampler body.

In the embodiment where the sampler operates as a "basic", "non-smart" device, and a separate smart device 2000 is provided, the one or more forms of animal ID which may be sensed or captured by the smart device may either be stored on the smart device, for immediate or deferred transmission to a desired repository, such as the laboratory, or may be transmitted to and stored on the associated collecting device 250 or punch 251.

Figure 7:
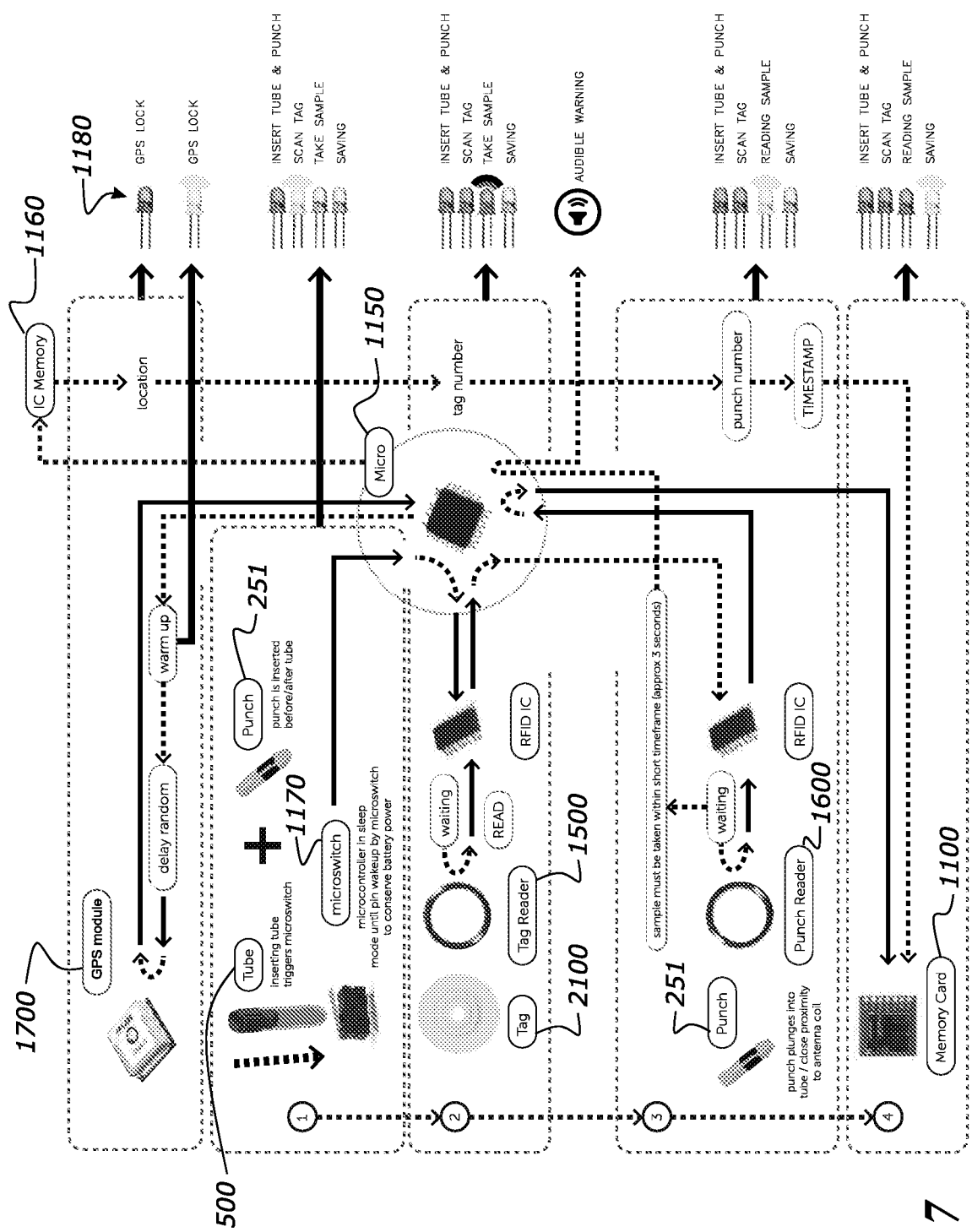
FIG. 7 is a flowchart illustrating components (and associated operations) of a sampler according to one embodiment.
Figure 8:
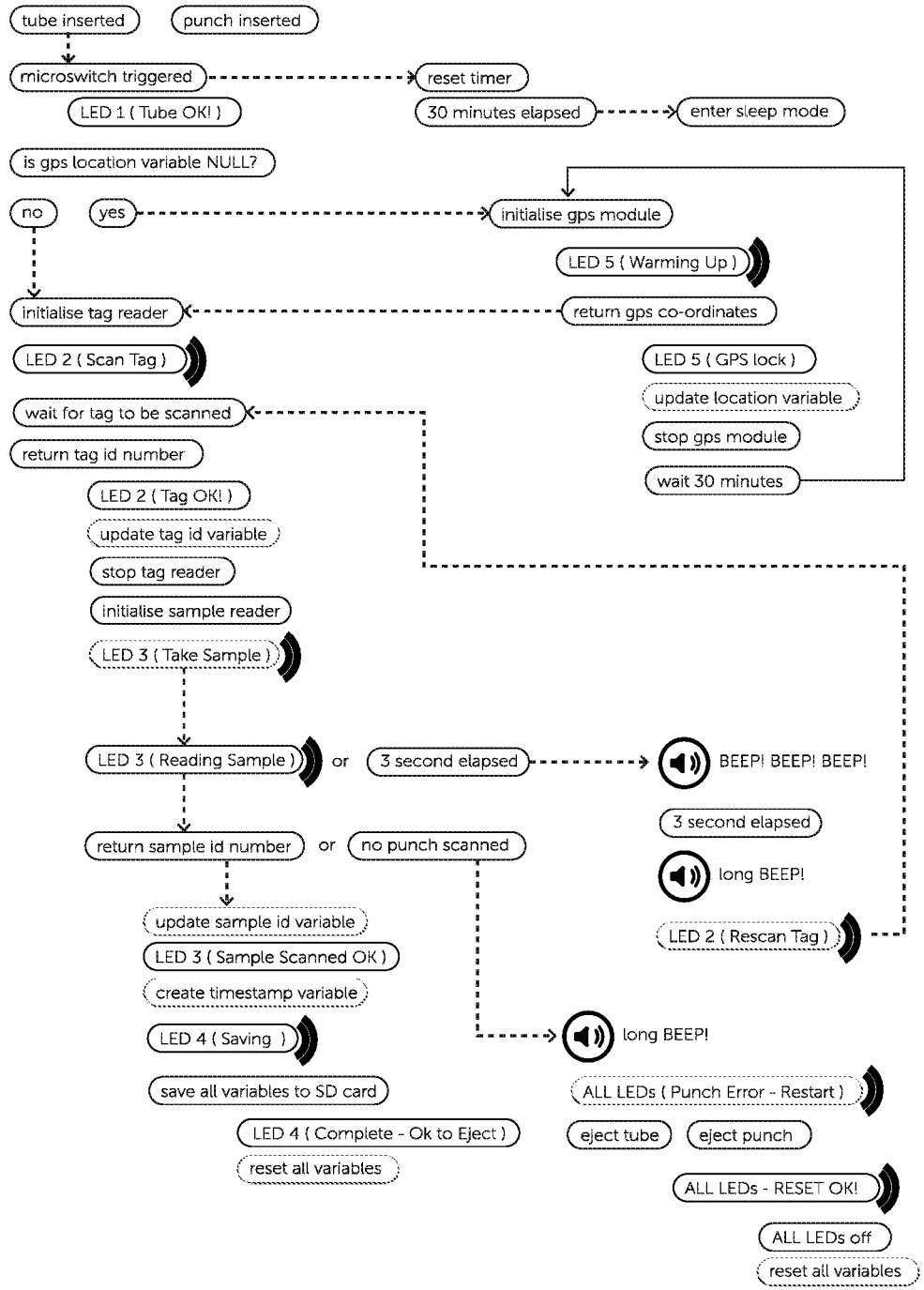
FIG. 8 is a flowchart illustrating steps of a sampling process according to one embodiment.

FIGS. 7 and 8 are schematic flow charts that detail particular exemplary embodiments of the sampling device and the sampling process. It will be appreciated that the steps and sequencing depicted in these flow charts are provided for explanatory purposes. Accordingly, any one or more of the components or steps described may be modified or eliminated, and/or the steps of the process may be rearranged in a different order as appropriate without departing from the scope of the invention.

With reference to FIGS. 7 and 8, processing unit such as microprocessor 1150 controls the operation of the sampler, such that on wake up (e.g., after accepting user credentials) it may first query the location coordinates of the sampler, by accessing GPS module 1700 (if provided). As discussed, alternatives to the GPS module may be other positional tracking or triangulation systems, acquired through user input.

In one example, the most recent location coordinates stored in microprocessor memory 1160 is used as the initial location variable, and this is periodically updated by the GPS module 1700. In some embodiments, while the GPS module is searching for location data, an LED 1180 or other audio, visual or haptic feedback component on the sampler 1, 1', 1", 1'" returns a signal that the GPS is locked and/or warming up, so that the user is informed to wait until the GPS has successfully returned the GPS coordinates.

Once the GPS coordinates have been returned, the user may then insert a storage container 500 into the storage container holder 300. In some embodiments, inserting the storage container triggers a micro switch 1170 or other switch, which then triggers the next step of the operation (e.g., reading the animal tag). Triggering of the micro switch may help to conserve the battery of the sampling device (by turning the animal tag reader 1500 and/or sample ID reader 1600 off when not needed), and/or to ensure that the sample is taken only when a storage container 500 is in place.

In alternative embodiments, the storage container 500 may be inserted before or while the GPS module or other positioning technology is obtaining the GPS coordinates or other location information. In this case, a micro switch need not be provided, and the sampler may be ready to use as soon as the GPS coordinates have been obtained. It will also be appreciated that the GPS requirement may be overridden by an authorised user, e.g., for use in locations where GPS signals may be weak or unavailable. It is preferable that the override to allow sampling to continue without location data is only able to be operated when the signal or information required to determine positioning is not available, or is below a desired threshold, for a predetermined period of time, or by a user having sufficient privileges.

In high-risk environments it may be preferable to omit the override, so that the sampling may not continue without location data being provided. In such a situation, in order to ensure that the sampler is able to be used in the maximum number of physical locations, such as indoors or where there is legitimately no capacity to acquire location data, it may be preferable to provide the sampler with multiple positioning technologies, or provide alternative forms of animal ID that must be provided in place of the location data. Where alternative forms of animal ID may be provided, it is preferable that they are only available after a predetermined time has passed with no location data being able to be acquired.

In some embodiments where a magazine of collecting devices is not provided, e.g., as shown in FIG. 2, a new collecting device 250 or punch 251 must be individually inserted before taking the next sample. The collecting device/punch may be inserted into the sampler 1 either before or after the storage container 500 has been inserted into the storage container holder 300.

In other embodiments where a magazine of collecting devices is provided in the sampler, e.g., as shown in FIG. 1, the user may actuate (e.g., rotate) the magazine to position a new collecting device 250 in place, either before or after the storage container 500 has been inserted into the storage container holder.

Corresponding visual, audio or haptic feedback, e.g., via LED 1180 may be provided to prompt the user to insert the tube 500 and/or collecting device/punch, and subsequently to notify the user that the device is ready to scan the animal tag 2100.

The user then scans/captures the animal ID (e.g., via RFID, or by taking a picture or barcode scan) and the animal ID is stored in memory 1160. At this stage, a timer may be activated which starts the countdown to the predetermined time limit during which the sample has to be taken. This countdown may be indicated to the user via audio, visual or haptic feedback.

The user then takes the sample, e.g., by activating the trigger/handle of the sampler 1, 1', 1", 1'" to drive the punch 251 or collecting device 250 across or through the item or animal to remove the sample, and then into the storage container 500. As the punch 251 or collecting device 250 passes through the sample ID reader 1600, the ID of the punch 251 or collecting device 250 is read and stored in memory, e.g., memory storage 1100 of reader unit. A time stamp may be recorded simultaneously, or at any other time during the sampling process, as long as the time stamp is unambiguously associated with the individual sample taken.

If however, the sample is not taken within the time limit set by the timer, the microprocessor 1150 may initialise any one or more of the following responses. In one embodiment, a warning may be displayed to the user via visual, audio or haptic feedback. Micro switch 1170 may then switch off and the user is prompted to enter a password (or other response, e.g., remove the storage container and reposition it in place in the storage container holder 300) to reactivate the micro switch. This may then reactivate the animal tag reader 1500 and the user is then prompted to rescan the animal tag and subsequently take the sample within the time limit.

In another embodiment, after the visual, audio or haptic warning is activated, the user may be prompted to rescan the animal tag, and the rescanned ID replacing the original ID variable in memory 1160. Subsequently the user may then take the animal sample within the time limit.

In another embodiment, after the visual, audio or haptic warning is activated, the user may continue to take the sample, but a data warning tag is generated, linked to the sample, and stored in memory. This way, when the data is processed subsequently, the analyst will be alerted to the fact that that particular sample was taken outside of the prescribed time limit. This step of generating a data warning tag may be applied to any of the above response processes.

In another embodiment, a first time stamp is recorded at the time when the animal ID is captured and a second time stamp recorded at the time the sample is taken (or vice versa depending on the sampling procedure, i.e., if the user is required to first take a sample before recording the animal ID, a first time stamp may be recorded as the sample is taken, and the second time stamp recorded when the animal ID is captured). At the laboratory, the time stamp data may be analysed to flag which (if any) samples were processed outside of the required time limit.

The time stamp recording may additionally or alternatively be used to record other steps of the sampling process, e.g., recording of sample ID, sealing of the sample tube, entering and authentication of user credentials, and the time duration between any two steps may be analysed (whether directly by the processor on the reader unit, or at the laboratory).

In one embodiment, a warning may also be provided if the ID of the punch 251 or collecting device 250 is not successfully obtained. This may occur, for example if the magazine of collecting devices is empty and needs to be refilled, or if the RFID of the punch or collecting device 250 was not properly scanned/captured. In such cases, a visual, audio or haptic warning may be activated, and the user may be prompted to insert a new collecting device 250, and restart the entire sampling process.

In some embodiments where the sample tube 500 is sealed with a seal 260 in a two-step process, as described in relation to sampler 1''' above, the time between taking the sample and sealing the sample tube 500 may additionally or alternatively be restricted. That is, the or another timer may be activated (or a second time stamp recorded) when the sampler 1''' is actuated to drive the collecting device 250 and take the sample. The timer may stop or a time stamp recorded when the sampler 1''' is actuated to drive the seal into the sample tube 500, and if this step is not within a pre-set time limit, this may trigger one or more responses, e.g., deactivation of the sampler, audio, visual, haptic feedback, as described above in relation to the duration between capturing of animal ID and taking the sample.

Alternatively, as described above, if the time between taking a sample and sealing the sample tube exceeds the time limit, a warning data tag may be recorded and reviewed at the laboratory.

Alternatively, a first time stamp may be recorded when the sample is taken and/or a first time stamp may be recorded when the animal ID is captured, a second time stamp recorded when the sample tube is capped, and the time stamp data associated with the sample in memory, to be subsequently analysed at the laboratory.

In preferred embodiments, each sample taken has an associated record of data, which may be stored in memory or transmitted to an external device. The record of data comprises at least i) the animal ID and ii) sample identification information. In some embodiments, the sample identification information is associated with the collecting device and/or storage container (e.g., via machine readable code or EID on the collecting device and/or storage container). In other embodiments, the sample identification information could be a linked to the specific order in which an ordered/numbered array of collecting devices and/or storage containers is provided to the sampler.

In some embodiments, the record of data further comprises additional information associated with the sample as described above, e.g., time stamps, data warning tags, photographs, GPS data, user credentials, Accordingly, each sample may be automatically associated with a record of multiple pieces of information related to the particular sample, to improve the efficiency and security of the sampling process and prevent fraud.

Once the full sampling process for one animal is completed, the data stored in the microprocessor memory 1160 may be transferred to memory storage 1100. The device may then be initialised for the next sample, e.g., the microprocessor memory 1160 may be erased. To conserve battery, the microprocessor may put the device into sleep or standby mode if the sampler is not used for a predetermined time period, e.g., 30 minutes. Upon wake up (which may be performed via user login, activating a switch, inserting the storage container 500) the microprocessor may activate GPS module 1700 to update the GPS coordinates, as discussed above.

Where a visual, audio or haptic feedback or warning is indicated in the description above, it should be understood that the feedback may be unique to the particular event or a set of related events, e.g., a specific LED colour, a specific number or pattern of audio beeps, to help the user identify the exact issue/event that is occurring. In another example, the feedback or warning may be displayed on the user interface of a connected device, e.g., smartphone 2000.

The foregoing description of the invention includes preferred forms thereof. Modifications may be made thereto without departing from the scope of the invention.

The invention claimed is:

1. A system for taking and removing a sample that is a biological sample from an animal, the system comprising
    A) a sampler comprising
        a handheld body including and holding:
            i. a storage container holder adapted in use to accommodate a storage container capable of receiving and storing the sample,
            ii. a sample collecting device holder adapted in use to accommodate a sample collecting device, wherein a sample removing region exists between the storage container holder and the sample collecting device holder to accommodate an item that is an animal material from which the sample is to be taken,
            iii. an actuator adapted to drive the sample collecting device from the sample collecting device holder, to remove the sample from the item, and into the storage container, and
    B) a reader unit engaged with the handheld body and comprising:
        i. a sample identification reader adapted to capture identification information associated with the sample collecting device and/or the storage container, the identification information associated with the sample collecting device and/or the storage container defining a sample information, and
        ii. an animal identification reader adapted to capture identification information associated with the item from which the sample is to be taken, the identification information associated with the item from which the sample is to be taken defining an animal identification, wherein the reader unit is configured to measure and/or record time between:
 a) capturing the animal identification and taking the sample, and/or
 b) taking the sample and capturing the animal identification to compare the measured and/or recorded time against a predetermined time, wherein, if said measured and/or recorded time exceeds the predetermined time, the handheld body or the reader unit provides at least one of audio, visual and haptic feedback to a user of the sampler.

2. A sampler comprising
A) a handheld body including and holding:
 a. a storage container holder adapted in use to accommodate a storage container capable of receiving and storing a sample that is a biological sample,
 b. a sample collecting device holder adapted in use to accommodate a sample collecting device, wherein a sample removing region exists between the storage container holder and the sample collecting device holder to accommodate an item that is an animal material from which the sample is to be taken,
 c. an actuator adapted to drive the sample collecting device from the sample collecting device holder, to remove the sample from the item, and into the storage container, and
B) a reader unit engaged to said handheld body and comprising:
 i. a sample identification reader adapted to capture identification information associated with the sample collecting device and/or the storage container, the identification information associated with the sample collecting device and/or the storage container defining a sample information, and
 ii. an animal identification reader adapted to capture identification information associated with the item from which the sample is to be taken, the identification information associated with the item from which the sample is to be taken defining an animal identification,
wherein the reader unit is configured to measure and/or record time between:
 a) capturing the animal identification and taking the sample, and/or
 b) taking the sample and capturing said animal identification
to compare the measured and/or recorded time against a predetermined time, wherein, if said measured and/or recorded time exceeds the predetermined time, the handheld body or the reader unit provides at least one of audio, visual and haptic feedback to a user of the sampler.

3. The sampler of claim 2 wherein the reader unit comprises a transmitter to transmit the animal identification and/or the sample information to an external device.

4. The sampler of claim 2, wherein at least one of the storage container holder and the collecting device holder is/are permanently engaged to the handheld body.

5. The sampler of claim 2, wherein the sample information to be read by the sample identification reader comprises one or more of a machine readable identification and an electronic identification associated with the collecting device and/or storage container.

6. The sampler of claim 2, wherein the animal identification to be read by the animal identification reader comprises one or more of a machine readable identification and an electronic identification associated with the item from which the sample is to be taken.

7. The sampler of claim 2, wherein each reader is configured to capture respective identification information via compatible electronic identification communication.

8. The sampler of claim 7, wherein each of the sample identification reader and the animal identification reader utilizes different frequencies for the electronic identification communication.

9. The sampler of claim 2, wherein the reader unit comprises a camera configured for one or more of:
 a) capturing the sample information,
 b) capturing the animal identification,
 c) obtaining supplemental data relating to one or more of:
  i) the item to be sampled,
  ii) a location of sampling, and
  iii) a sampling procedure.

10. The sampler of claim 2, wherein the reader unit comprises a tag reader, wherein the reader unit records a time stamp at a time when said animal identification is captured, and wherein the reader unit records another time stamp at a time the sample is taken.

11. A method of taking a sample that is a biological sample from an item that is a plant material or an animal material and placing the sample into a storage container using a sampler, the sampler comprising:
 a handheld body presenting:
  a storage container holder adapted in use to accommodate the storage container for receiving the sample,
  a sample collecting device holder adapted in use to accommodate a sample collecting device,
  a sample removing region provided between the storage container holder and the sample collecting device holder to accommodate the item from which the sample is to be taken, and
  an actuator adapted to drive the sample collecting device from the sample collecting device holder, to remove the sample from the item, and into the storage container; and
 an identification reader adapted to capture identification information associated with the item from which the sample is to be taken, the identification information associated with the item from which the sample is to be taken defining an item identification;
the method comprising:
 a) supplying the sampler with the storage container and the sample collecting device at the storage container holder and the sample collecting device holder respectively,
 b) driving the actuator to remove the sample from the item,
 c) capturing the item identification,
wherein the method further comprises monitoring a sampling time duration that is a time duration between steps (b) and (c) and/or recording a time stamp at the time of each of steps (b) and (c) regardless of whether step (b) occurs before or after step (c), and comparing the sampling time duration with a predetermined time limit, and at least one of audio, visual and haptic feedback is provided to a user if said sampling time duration is longer than said predetermined time limit.

12. The method of claim 11, further comprising prompting the user to restart a sampling process if the sampling time duration is longer than the predetermined time limit.

13. The method of claim 11, wherein the sampling time duration when step (b) occurs after step (c) is monitored such that if the sampling time duration exceeds said predetermined time limit, said driving of the actuator is prevented by said sampler.

14. The method of claim 13, wherein, if the sampling time duration is longer than the predetermined time limit and the sampler is deactivated by preventing the actuator from being actuated, the user must perform one or more authorization steps comprising one or more of inputting user login details and capturing user credentials, and/or restarting a sampling process to reactivate the sampler.

15. A sampling system comprising
(i) a handheld body including and holding:
  a. a storage container holder adapted in use to accommodate a storage container capable of receiving and storing a sample that is a biological sample from a biological item,
  b. a sample collecting device holder adapted in use to accommodate a sample collecting device, wherein a sample removing region exists between the storage container holder and the sample collecting device holder to accommodate an item from which the sample is to be taken,
  c. an actuator adapted to drive the sample collecting device from the sample collecting device holder, to remove the sample from the item, and into the storage container,
(ii) a sample identification reader adapted to capture identification information associated with the sample collecting device and/or the storage container, the identification information associated with the sample collecting device and/or the storage container defining sample information, and
(iii) an item identification reader adapted to capture identification information associated with the item from which the sample is to be taken, the identification information associated with the item from which the sample is to be taken defining an item identification,
wherein the system is configured to measure and/or record time between:
  a. capturing the item identification and capturing the sample information, and/or
  b. capturing the sample information and capturing the item identification,
and to compare the measured and/or recorded time against a predetermined time, wherein if said measured and/or recorded time exceeds the predetermined time the handheld body provides at least one of audio, visual and haptic feedback to a user of the sampling system, and
wherein the sample identification reader and the item identification reader together or severally form part of one of said handheld body and a handheld portable electronic device.

* * * * *